(12) United States Patent
Wentland

(10) Patent No.: US 8,263,807 B2
(45) Date of Patent: Sep. 11, 2012

(54) QUATERNARY OPIOID CARBOXAMIDES

(75) Inventor: Mark P. Wentland, Menands, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 974 days.

(21) Appl. No.: 12/188,814

(22) Filed: Aug. 8, 2008

(65) Prior Publication Data

US 2009/0197905 A1    Aug. 6, 2009

Related U.S. Application Data

(60) Provisional application No. 60/954,960, filed on Aug. 9, 2007.

(51) Int. Cl.
| C07C 233/00 | (2006.01) |
| C07C 235/00 | (2006.01) |
| C07C 237/00 | (2006.01) |
| C07C 239/00 | (2006.01) |
| C07C 211/00 | (2006.01) |
| A01N 33/12 | (2006.01) |
| A61K 31/14 | (2006.01) |

(52) U.S. Cl. .................. 564/163; 564/282; 514/642
(58) Field of Classification Search .................. 564/163, 564/282; 514/642
See application file for complete search history.

(56) References Cited

U.S. PATENT DOCUMENTS

| 4,032,529 | A | 6/1977 | Wentland et al. |
| 4,176,186 | A | 11/1979 | Goldberg et al. |
| 4,489,079 | A | 12/1984 | Giudice et al. |
| 6,784,187 | B2 | 8/2004 | Wentland |
| 2005/0176645 | A1 | 8/2005 | Mickle et al. |
| 2005/0182258 | A1 | 8/2005 | Schmidhammer et al. |
| 2006/0014771 | A1 * | 1/2006 | Cantrell et al. ............... 514/282 |
| 2006/0030580 | A1 | 2/2006 | Wentland |
| 2007/0021457 | A1 | 1/2007 | Wentland |

FOREIGN PATENT DOCUMENTS

| DE | 2254298 | 5/1974 |
| ES | 2121553 | 11/1998 |
| GB | 874217 | 8/1961 |
| JP | 40010154 | 5/1965 |
| WO | 97/25331 | 7/1997 |
| WO | WO 01/37785 | 5/2001 |
| WO | 02/36573 | 5/2002 |
| WO | WO 2004/005294 | 1/2004 |
| WO | WO 2006/096626 | 9/2006 |
| WO | 2007/022535 | 2/2007 |

OTHER PUBLICATIONS

Wentland et. al., Bioorganic and Medicinal Chemistry Letters, 2005, Elsevier, vol. 15, pp. 2107-2110.*
Bianchi, et al., "Quaternary narcotic antagonists' relative ability to prevent antinociception and gastrointestinal transit inhibition in morphine-treated rats as an index of peripheral selectivity"; Life Sciences (1982), 30(22), pp. 1875-1883.
Huidobro-Toro, et al., Comparative Study on the Effect of Morphine and the Opioid-Like Peptides in the Vas Deferens of Rodents: Species and Strain Differences, Evidence for Multiple Opiate Receptors, Life Sciences (1981), vol. 28, pp. 1331-1336.
Simpkins et al., "Evaluation of the sites of opioid influence on anterior pituitary hormone secretion using a quaternary opiate antagonist"; Neuroendocrinology (1991), 54(4), pp. 384-390.
Bianchetti, et al., "Quaternary derivatives of narcotic antagonists: sterochemical requirements at the chiral nitrogen for in vitro and in vivo activity"; Life Sciences (1983), 33 (Suppl. 1), pp. 415-418.
Wentland et al., "Redefining the structure-activity relationships of 2,6-methano-3-benzazocines. Part 3: 8-Thiocarboxamido and 8-thioformamido derivatives of cyclazocine", Bioorganic & Medicinal Chemistry Letters, vol. 15, No. 10, pp. 2547-2551 (2005).
International Search Report and Written Opinion for PCT/US2008/072632, (Dec. 29, 2008).

* cited by examiner

Primary Examiner — Sreeni Padmanabhan
Assistant Examiner — Sarah Pihonak
(74) Attorney, Agent, or Firm — Heslin Rothenberg Farley & Mesiti PC

(57) ABSTRACT

Compounds of formulas:

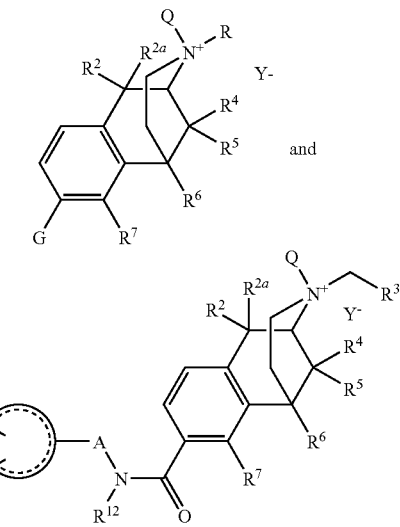

are disclosed. The compounds are useful for ameliorating the side effects of therapeutic opiates.

2 Claims, 10 Drawing Sheets

IP

PO

QUATERNARY OPIOID CARBOXAMIDES

CROSS REFERENCE TO RELATED APPLICATIONS

This application claims priority of U.S. provisional application 60/954,960, filed Aug. 9, 2007, the entire disclosure of which is incorporated herein by reference.

FEDERALLY SPONSORED RESEARCH

The following invention was made with government support under contract number R01 DA12180 awarded by the National Institutes of Health (NIH)/National Institute on Drug Abuse (NIDA). The Government has certain rights in this invention.

JOINT RESEARCH AGREEMENT

Inventions described in this application were made by or on behalf of Mark Wentland, Rensselaer Polytechnic Institute and Alkermes, Inc, who are parties to joint research agreements that were in effect on or before the date such inventions were made and such inventions were made as a result of activities undertaken within the scope of the joint research agreement.

FIELD OF THE INVENTION

The invention relates to opioid receptor binding compounds that are useful to ameliorate the peripheral side effects of therapeutic opiates.

BACKGROUND OF THE INVENTION

Opiates have been the subject of intense research since the isolation of morphine in 1805, and thousands of compounds having opiate or opiate-like activity have been identified. Many opioid receptor-interactive compounds including those used for producing analgesia (e.g., morphine) and those used for treating drug addiction (e.g., naltrexone and cyclazocine) in humans have limited utility due to poor oral bioavailability and a very rapid clearance rate from the body. This has been shown in many instances to be due to the presence of the 8-hydroxyl group (OH) of 2,6-methano-3-benzazocines, also known as benzomorphans [(e.g., cyclazocine and EKC (ethylketocyclazocine)] and the corresponding 3-OH group in morphinanes (e.g., morphine).

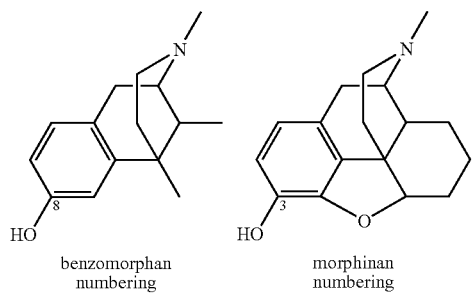

benzomorphan numbering morphinan numbering

The high polarity of these hydroxyl groups retards oral absorption of the parent molecules. Furthermore, the 8-(or 3-)OH group is prone to sulfonation and glucuronidation (Phase II metabolism), both of which facilitate rapid excretion of the active compounds, leading to disadvantageously short half-lives for the active compounds. Until the publications of Wentland in 2001, the uniform experience in the art of the past seventy years had been that removal or replacement of the 8-(or 3-) OH group had led to pharmacologically inactive compounds.

U.S. Pat. No. 6,784,187 (to Wentland) disclosed that the phenolic OH of opioids could be replaced by $CONH_2$. In the cyclazocine series of opioids, it was shown that 8-carboxamidocyclazocine (8-CAC) had high affinity for µ and κ opioid receptors. In studies in vivo, 8-CAC showed high antinociception activity and a much longer duration of action than cyclazocine (15 h vs. 2 h) when both were dosed at 1 mg/kg ip in mice.

Quaternary derivatives of the opioid antagonist naltrexone have been disclosed for preventing or relieving the intestinal mobility inhibiting side effects of narcotic analgesics such as morphine and related opiates without impairing the analgesic activity of the narcotic analgesic. Methylnaltrexone, for example, was disclosed in U.S. Pat. No. 4,176,186 (to Goldberg et al.). However, the dose required to prevent or inhibit intestinal motility inhibiting side effects is relatively high. Thus, a need exists to develop compounds with increased activity at lower doses.

SUMMARY OF THE INVENTION

We have now found that derivatives of quaternary naltrexone salts can be made that replace the 8-(or 3-)hydroxyl group by a number of small, polar, neutral residues (defined herein to exclude hydroxy and lower alkoxy) such as carboxamide, thiocarboxamide, hydroxyamidine and formamide groups. Moreover, we have also found that the nitrogen of the carboxamide can be substituted with fairly large and relatively non-polar groups. All of such compounds exhibit excellent opioid binding and possess good to excellent peripheral opioid antagonism activity. Not only do the benzomorphan, morphinan carboxamides described herein have high affinity for opioid receptors, compounds containing small, polar, neutral residues such as carboxamide, thiocarboxamide, hydroxyamidine and formamide groups described herein in place of OH are long acting, far less susceptible to Phase II metabolism and generally more orally bioavailable.

The compounds of the invention are useful for ameliorating the side effects of therapeutic opiates. These include constipation, nausea/vomiting (emesis), cough suppression, pruritis, dysphoria and urinary retention. The compounds of the invention may also be useful for improving post-operative bowel function that may or may not be related to opioid treatment.

In one aspect, the invention relates to 2,6-methano-3-benzazocine-8-carboxamides and 2,6-methano-3-benzazocine-8-carboxamide derivatives of formula:

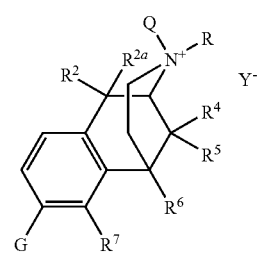

wherein

G is selected from polar, neutral residues and, in particular, can be selected from the group consisting of substituted or unsubstituted amide groups, including but not limited to carboxamide, thiocarboxamide, acylamine and formamide groups; substituted or unsubstituted amines; substituted or unsubstituted amidines, such as hydroxyamidines; and alkyls substituted by polar neutral residues. Preferably G can be selected from $CONH_2$ and $CSNH_2$.

For example, G can be —$CH_2Z$ (where Z is a polar neutral residue, such as $CH_2OR_a$, $CH_2NR_bR_c$), —CN, —$NR_bSO_2$—$R_c$, —C(=W)$R_a$, —$NR_aCOR_b$, —$NR_aCSR_b$, —$SO_2NR_bR_c$, —$NR_b$-$Q_a$-$R_c$, (C=W)$NR_bR_c$, C(O)$OR_a$, heterocycle, substituted heterocycle, heteroaryl, and substituted heteroaryl, such as

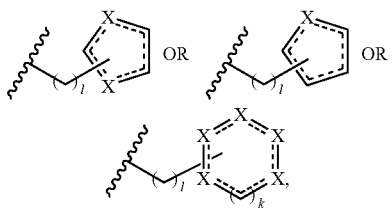

wherein l is 0, 1, 2, 3, 4 or 5; k is 0, 1 or 2; X is C, N, S or O and ===== represents a single or double bond;

$R_a$, $R_b$, $R_c$ are each independently selected from:
hydrogen;
aryl; substituted aryl; heteroaryl; substituted heteroaryl; heterocyclic or substituted heterocyclic; and
substituted or unsubstituted alkyl, alkenyl, alkynyl, cycloalkyl, or cycloalkenyl each containing 0, 1, 2, or 3 or more heteroatoms selected from O, S, or N;
alternatively, $R_a$, $R_b$ and $R_c$ taken together with the attached atom form a heterocyclic or substituted heterocyclic;
$Q_a$ is absent or selected from (C=O), ($SO_2$), (C=NH), (C=S), or ($CONR_a$);
W is O, S, $NOR_a$ or $NR_a$;
Y is a pharmaceutically acceptable counterion; for example, Y can be tartrate, citrate, chloride or methansulfonate;
Q is a substituted or unsubstituted, saturated or unsaturated aliphatic or aromatic group, such as a substituted or unsubstituted, saturated or unsaturated alkyl (for example, $C_1$-$C_{20}$-alkyl), alkenyl (for example, $C_2$-$C_{20}$-alkenyl), alkynyl (for example, $C_2$-$C_{20}$-alkynyl) aryl, heteroaryl, heterocyclyl, arylalkyl (for example, where aryl is $C_6$-$C_{10}$-aryl and alkyl is $C_1$-$C_{20}$-alkyl), arylalkenyl, arylalkynyl or heteroarylalkyl (for example benzyl). In one embodiment, Q is an alkyl or benzyl;
$R^2$ and $R^{2a}$ are independently hydrogen, alkyl, aryl, arylalkyl, heteroaryl, hydroxy, amino, or alkoxy (preferably hydrogen) or taken together $R^2$ and $R^{2a}$ are =O;
R is chosen from hydrogen or a substituted or unsubstituted, saturated or unsaturated aliphatic or aromatic group, including lower alkyl, alkenyl, aryl, heterocyclyl, benzyl, hydroxyalkyl and —$CH_2R^3$;
$R^3$ is chosen from hydrogen, lower alkyl, alkenyl, aryl, heterocyclyl, benzyl and hydroxyalkyl, including cycloalkyl and vinyl;
$R^4$ is chosen from hydrogen, hydroxy, amino, lower alkoxy or a substituted or unsubstituted, saturated or unsaturated aliphatic or aromatic group, including $C_1$-$C_{20}$ alkyl and $C_1$-$C_{20}$ alkyl substituted with hydroxy or carbonyl (e.g., oxo), preferably hydrogen and 3-oxo-5-cyclopentyl-1-pentanyl;
$R^5$ is hydrogen or a substituted or unsubstituted lower alkyl, preferably unsubstituted lower alkyl, preferably methyl or ethyl;
$R^6$ is a substituted or unsubstituted lower alkyl, preferably unsubstituted lower alkyl, preferably methyl or ethyl;
$R^7$ is chosen from hydrogen, hydroxy, amino, lower alkoxy, or a substituted or unsubstituted, saturated or unsaturated aliphatic or aromatic group, preferably hydrogen or hydroxy;
or together G, $R^4$, $R^5$, $R^6$ and/or $R^7$ may form from one to three rings or more, said rings having optional additional substitution, and/or
together Q and $R^3$ may form from one to three rings or more, said rings having optional additional substitution, and/or
together Q and $R^2$ may form from one to three rings or more, said rings having optional additional substitution.

Subclasses of the foregoing structure include:
II. 2,6-methano-3-benzazocines of the structure shown above, in which $R^4$, $R^5$, $R^6$ and $R^7$ do not form additional rings;

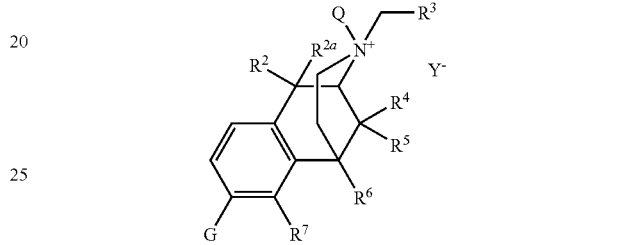

wherein G, Q, Y, $R^2$, $R^{2a}$, $R^3$, $R^4$, $R^5$, $R^6$ and/or $R^7$ are as defined above.

Preferably, $R^3$ is selected from hydrogen, cyclopropyl, cyclobutyl, phenyl, vinyl, dimethylvinyl, hydroxycyclopropyl, furanyl, and tetrahydrofuranyl;
$R^4$ is chosen from hydrogen, hydroxy, amino, lower alkoxy, $C_1$-$C_{20}$ alkyl and $C_1$-$C_{20}$ alkyl substituted with hydroxy or carbonyl;
$R^5$ is lower alkyl;
$R^6$ is lower alkyl; and
$R^7$ is chosen from hydrogen and hydroxyl.
IIIa. morphinans in which $R^5$ and $R^6$ form a ring and $R^7$ is hydrogen:

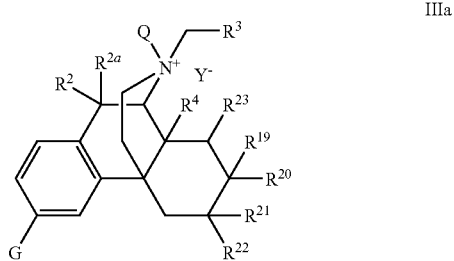

wherein G, Q, Y, $R^2$, $R^{2a}$, $R^3$, and $R^4$ are as defined above and $R^{19}$, $R^{20}$, $R^{21}$, $R^{22}$, and $R^{23}$ are hydrogen or a substituted or unsubstituted aliphatic or aromatic group or can be taken together to form a heterocyclic or carbocyclic ring.

Preferably, $R^{19}$ is hydrogen or lower alkyl;
$R^{20}$ is chosen from hydrogen, lower alkyl and hydroxy(lower alkyl);
$R^{21}$ is hydrogen;
$R^{22}$ is chosen from hydrogen, hydroxy, lower alkoxy and —$NR^{13}R^{14}$; or
together, $R^{21}$ and $R^{22}$ form a carbonyl (=O) or a vinyl substituent (=$CH_2$);
or, together, $R^4$ and $R^{21}$ form a ring;

$R^{13}$ and $R^{14}$ are chosen independently from hydrogen, $C_1$-$C_6$ alkyl and $C_1$-$C_6$ acyl; and $R^{23}$ is hydrogen, alkyl (e.g. methyl), or together $R^{19}$ and $R^{23}$ form a second bond.

IIIb. morphinans in which $R^5$ and $R^6$ form a ring and $R^7$ is hydroxy:

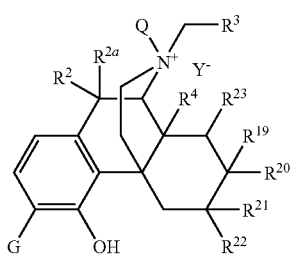

IIIb wherein G, Q, Y, $R^2$, $R^{2a}$, $R^3$, $R^4$, $R^{19}$, $R^{20}$, $R^{21}$, $R^{22}$, and $R^{23}$ are as defined above.

IV. morphinans in which $R^5$, $R^6$ and $R^7$ form two rings:

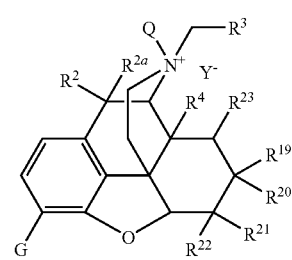

IV wherein G, Q, Y, $R^2$, $R^{2a}$, $R^3$, $R^4$, $R^{19}$, $R^{20}$, $R^{21}$, $R^{22}$, and $R^{23}$ are as defined above.

V. morphinans wherein $R^4$ and $R^{11}$ form an additional sixth ring, which may be saturated or unsaturated (but not fully aromatic):

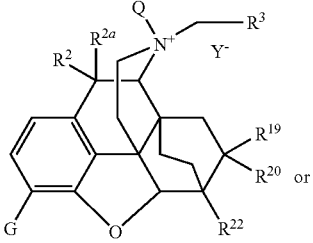

Va

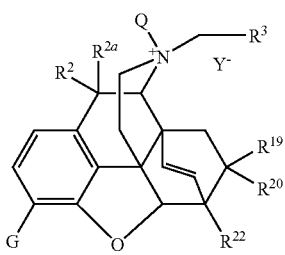

Vb wherein G, Q, Y, $R^2$, $R^{2a}$, $R^3$, $R^4$, $R^{19}$, $R^{20}$, $R^{21}$, $R^{22}$ and $R^{23}$ are as defined above.

In addition to the major subclasses, there are compounds which a person of skill in the art recognizes as closely related to the major subclasses, but which defy easy description in a common Markush structure, for example, compounds wherein one or more R groups (e.g., $R^4$, $R^5$, $R^6$ and/or $R^7$) possess a group of one of the above described formulae, thereby forming a dimeric or heterodimeric compound. As such, a "substituent" or ring formed by two or more variables is intended to include such dimeric and heterodimeric compounds. Alternatively or additionally, a substituent for one or more R groups can be a substituted morphinan group, such as naltrexone, methyl-naltrexone or a group selected from Charts 1-3 below, and the like.

In another aspect, the invention relates to compounds related to the foregoing in which G is of formula:

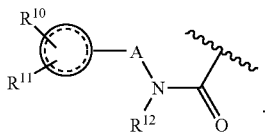

These compounds have the formulae:

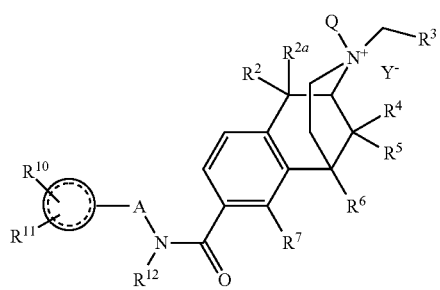

VI wherein

is an aryl or heteroaryl residue of one to three or more rings and

A is a bond or a linker, such as $(CH_2)_n$, wherein one or more $CH_2$ may be replaced by —O—, cycloalkyl or —$CR^{1a}R^{1b}$;

$R^{1a}$ and $R^{1b}$ are chosen independently from hydrogen, halogen, lower alkyl, lower alkoxy and lower alkylthio;

$R^{10}$ is hydrogen or one or two substituents, including, for example, residues chosen independently from hydrogen, hydroxyl, halogen, $(C_1$-$C_6)$alkyl, $(C_1$-$C_6)$alkoxy, halo($C_1$-$C_6$)alkyl and halo($C_1$-$C_6$)alkoxy and $(C_1$-$C_6$)alkylthio;

$R^{11}$ is H or

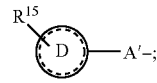

is an aryl or heteroaryl residue of one to three rings;
A' is a linker, such as $(CH_2)_m$, wherein one or more $CH_2$ may be replaced by —O—, cycloalkyl, —$CR^{1a}R^{1b}$—, —C(=O)— or —NH—;
$R^{12}$ is chosen from hydrogen and lower alkyl;
$R^{15}$ is one or two residues chosen independently from hydrogen, hydroxyl, halogen, $(C_1\text{-}C_6)$alkyl, $(C_1\text{-}C_6)$alkoxy, halo$(C_1\text{-}C_6)$alkyl and halo$(C_1\text{-}C_6)$alkoxy and $(C_1\text{-}C_6)$alkylthio;
m is zero or an integer from 1 to 6; and
n is an integer from 1 to 6; and
Q, Y, $R^2$, $R^{2a}$, $R^3$, $R^4$, $R^5$, $R^6$ and $R^7$ are as defined above. Preferably, Q is chosen from alkyl and benzyl.
In one embodiment, A is other than $CH_2$.

Subclasses of the foregoing structure (VI) include parallel classes to those outlined above, e.g. 2,6-methano-3-benzazocines in which $R^4$, $R^5$, $R^6$ and R7 do not form additional rings; morphinans in which R5 and R6 form one ring; morphinans in which R5, R6 and R7 form two rings; and morphinans in which R4 and R21 form a sixth ring, which may be saturated or unsaturated and so on.

DETAILED DESCRIPTION OF THE INVENTION

Figure 1:
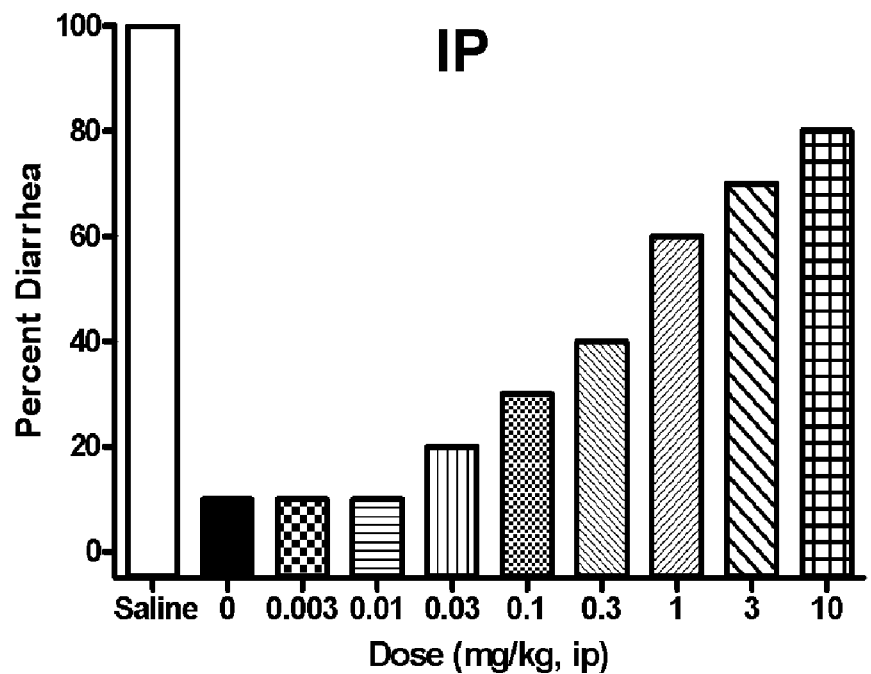
FIG. 1 is a graph of percent diarrhea vs. dose showing the inhibition of morphine blockade of $PGE_2$-induced diarrhea for mice treated with Compound 6 (intraperitoneal and oral administration).
Figure 1:
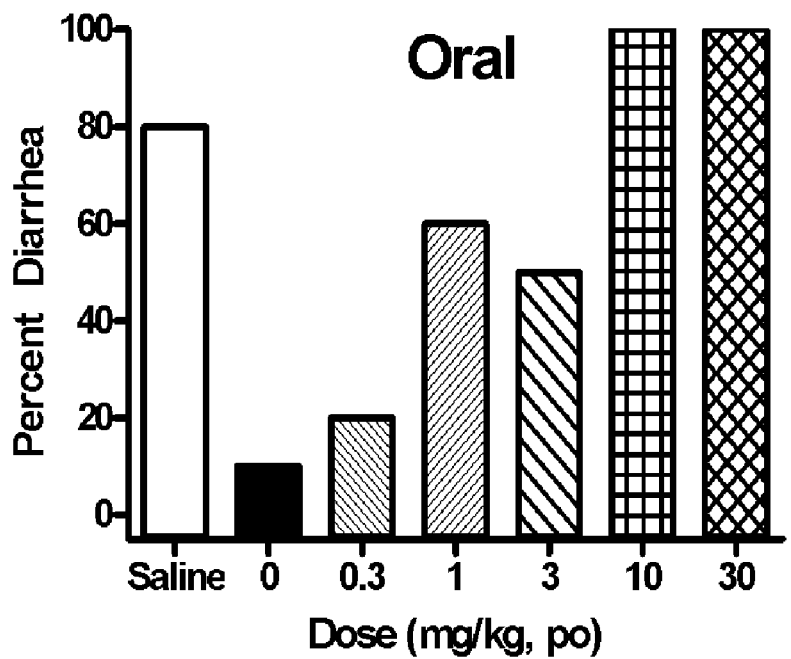

Phenolic hydroxyls of benzomorphan and morphinan derivatives can be chemically converted to carboxamides by a simple, flexible and convenient route described in U.S. Pat. Nos. 6,784,187 and 7,057,035, and in U.S. Patent Application Publication No. US 2007/0021457 A1, which are all incorporated herein by reference.

In one aspect the invention relates to compounds of formula

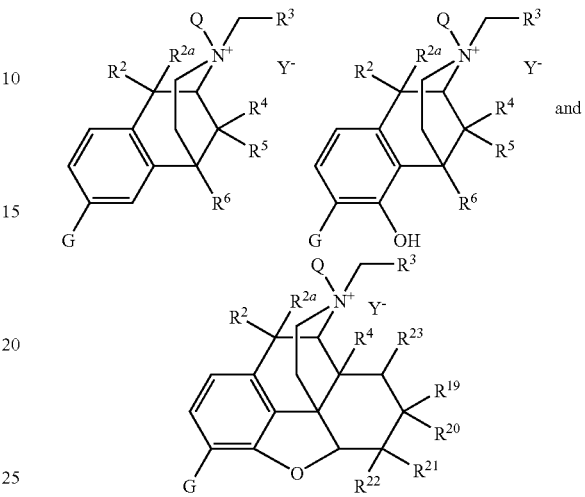

and various derivatives or modifications of these compounds.

In another aspect the invention relates to compounds of formula

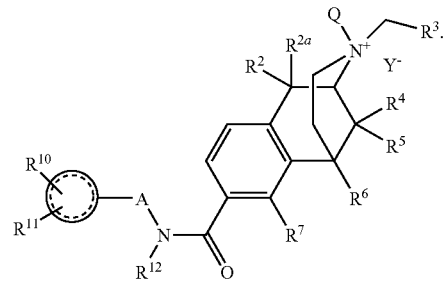

In one major subclass, $R^{11}$ is

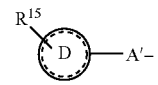

and the compounds are biphenyls, diaryl ethers and the like of formula:

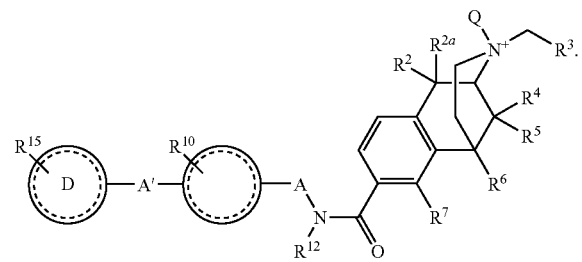

It is known in the art that compounds that are μ, δ and κ agonists exhibit analgesic activity; compounds that are selective μ agonists exhibit anti-diarrheal activity and are useful in treating dyskinesia; μ antagonists and κ agonists are useful in treating heroin, psychostimulant (i.e., cocaine, amphetamines), alcohol and nicotine addiction; κ agonists are also anti-pruritic agents and are useful in treating hyperalgesia. Recently it has been found [Peterson et al. *Biochem. Phar-* macol. 61, 1141-1151 (2001)] that κ agonists are also useful in treating retroviral infections. In general, the dextrorotatory isomers of morphinans of type III above are useful as antitussives and anticonvulsants.

Opioid receptor ligands having known high affinity are shown in the following charts. Replacement of OH with G in these compounds may produce compounds that exhibit similar activity and better bioavailability. The present invention further includes the quaternization of the following G-substituted compounds.

Chart 1. Opioid Receptor Ligands
Benzomorphinans (a.k.a. 2,6-Methano-3-benzazocines)

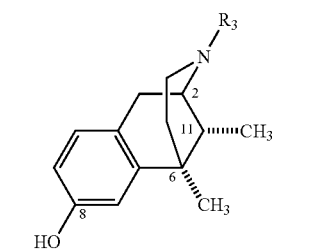

Cyclazocine, $R_3 = CH_2\text{-c-}C_3H_5$
Metazocine, $R_3 = CH_3$
Phenazocine, $R_3 = CH_2C_6H_5$
SKF 10,047, $R_3 = CH_2CH=CH_2$
Pentazocine, $R_3 = CH_2CH=C(CH_3)_2$
(all racemic)

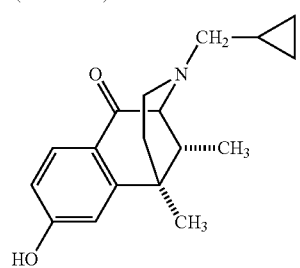

Ketocyclazocine

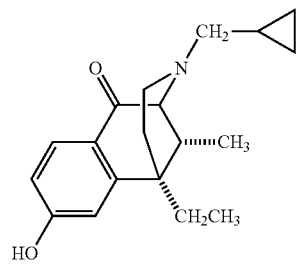

Ethylketocyclazocine (EKC)

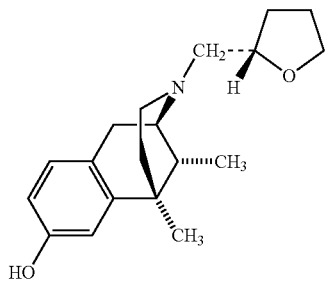

MR2034 - "Merz" core structure (opt. active)

-continued

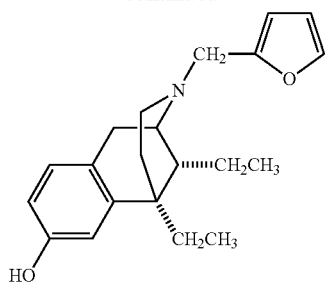

MR2266

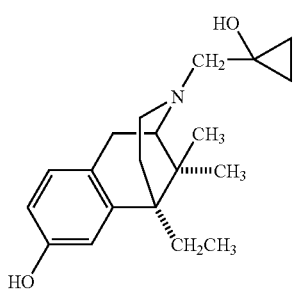

Bremazocine

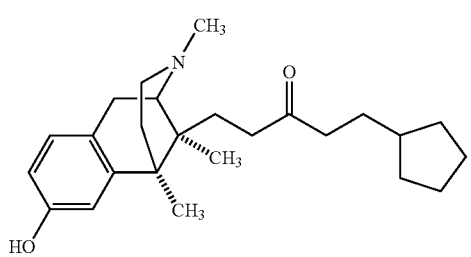

WIN 44,441

Chart 2. Opioid Receptor Ligands Morphine and Morphinans

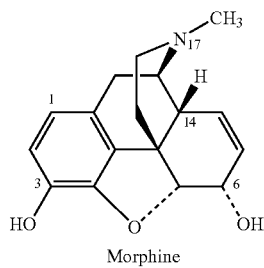

Morphine

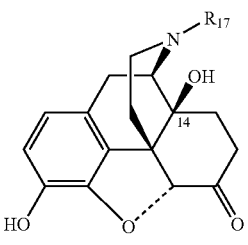

Naltrexone; $R^{17} = CH_2\text{-c-}C_3H_5$
Naloxone; $R_{17} = CH_2CH=CH_2$
Nalmexone; $R_{17} = CH_2CH=C(CH_3)_2$
Oxymorphone; $R_{17} = CH_3$ -continued
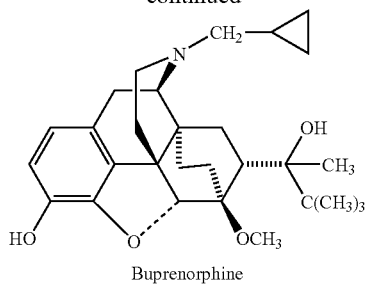
Buprenorphine
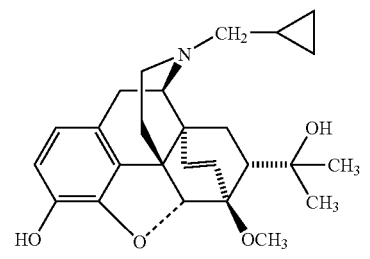
Diprenorphine
Etorphine (N-Me; n-Pr vs Me)
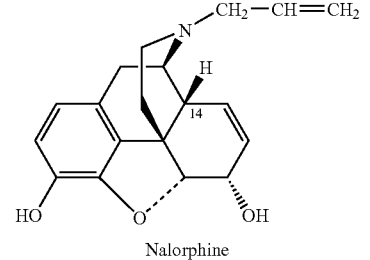
Nalorphine
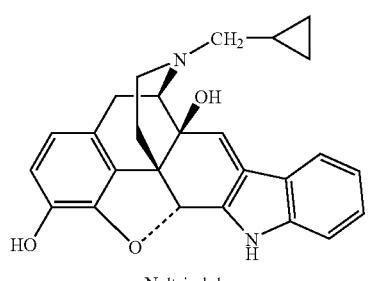
Naltrindole
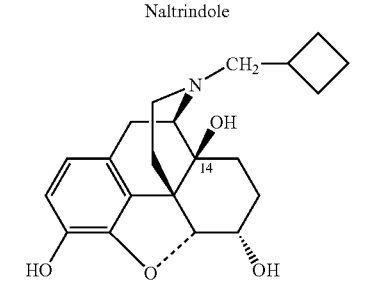
Nalbuphine
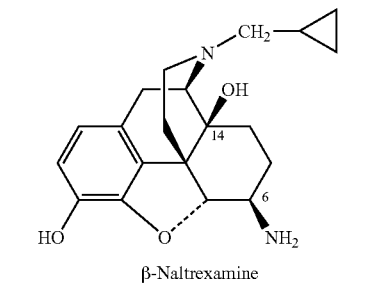
β-Naltrexamine
-continued
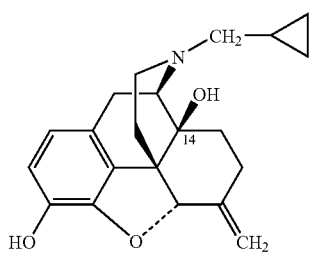
Nalmefene
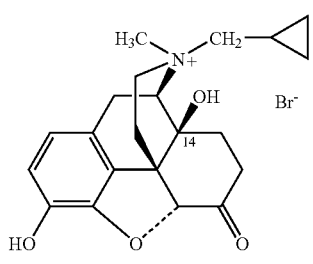
Methylnaltrexone
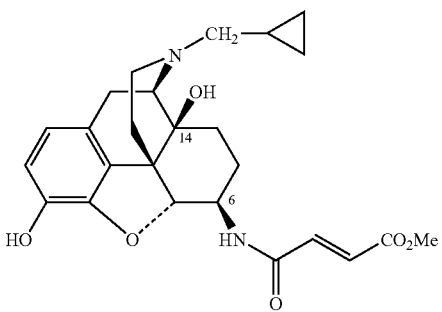
β-FNA
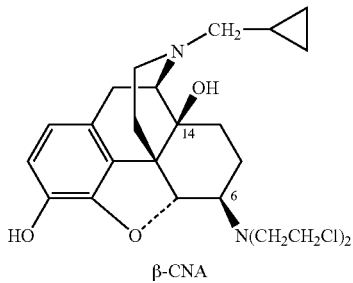
β-CNA
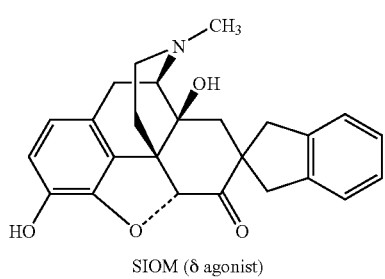
SIOM (δ agonist)

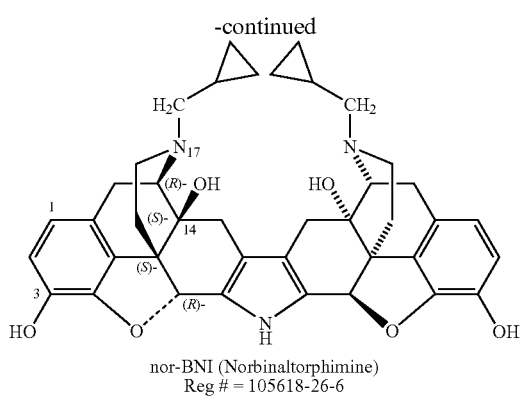

nor-BNI (Norbinaltorphimine)
Reg # = 105618-26-6

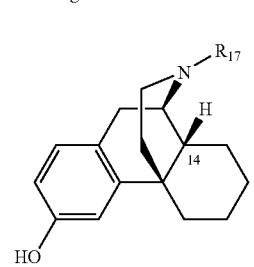

Levorphanol; $R_{17}$ = $CH_3$
Cyclorphan; $R_{17}$ = $CH_2$-c-$C_3H_5$
MCL 101; $R_{17}$ = $CH_2$-c-$C_4H_7$
Butorphanol; $R_{17}$ = $CH_2$-c-$C_4H_7$
and 14-OH
Merz-morphinane hybrid core; $R_{17}$ = $CH_2$-(S)-tetrahydrofurfuryl

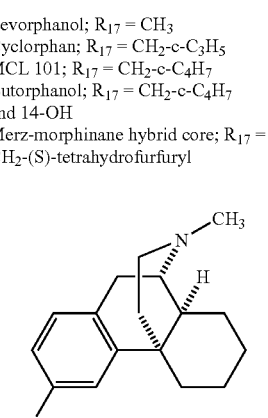

Dextromethorphan; R = $CH_3$
Dextrorphan; R = H
(note "opposite" sterochemistry)

Chart 3- Miscellaneous Opioid Receptor Ligands

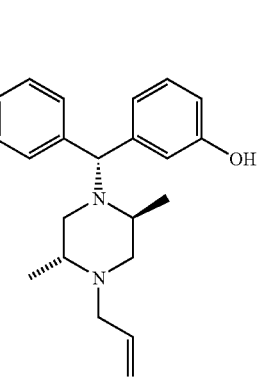

Registry Number 216531-48-5

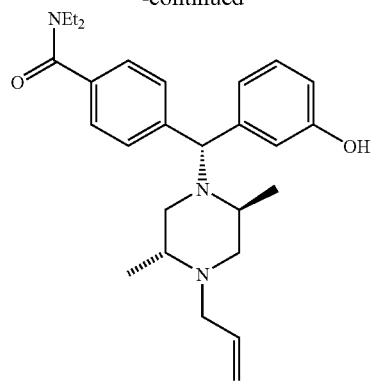

Registry Number 155836-52-5

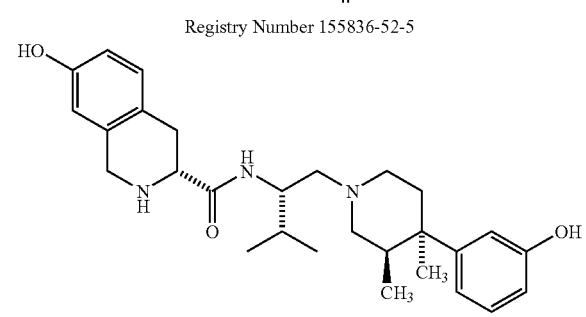

Registry number 361444-66-8

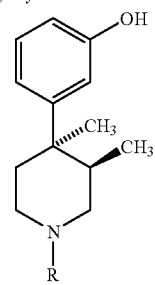

R = $CH_3$; Registry Number: 69926-34-7
R = $CH_2CH_2CH(OH)C_6H_{11}$; Registry Number 119193-09-8
R = $CH_2CH(CH_2Ph)CONHCH_2CO_2H$; Registry Number: 156130-44-8
R = $(CH_2)_3CH(CH_3)_2$; Registry Number: 151022-07-0
R = $(CH_2)_3$-2-thienyl; Registry Number: 149710-80-5

Meptazinol
Registry Number 59263-76-2

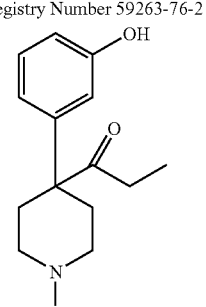

Ketobemidone
Registry Number 469-79-4

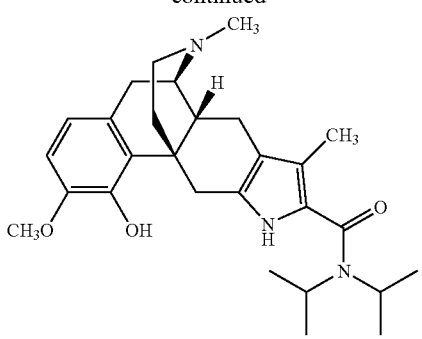

Registry number 177284-71-8

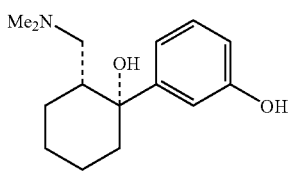

Tramadol active metabolite
Registry Number 80456-81-1

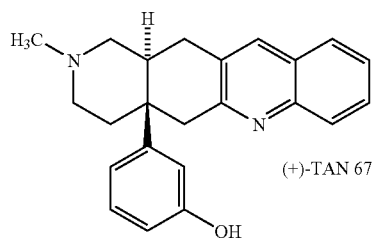

(+)-TAN 67

Registry number 189263-70-5

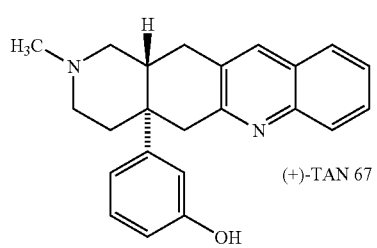

(+)-TAN 67

Registry number 173398-79-3

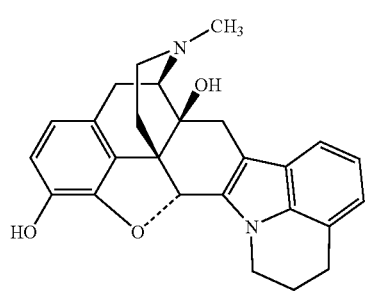

Registry number 189016-07-7

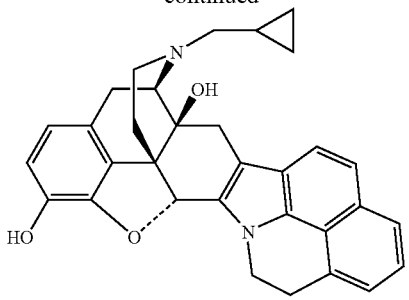

Registry number 189015-08-5

Other opioid receptor ligands are described in Aldrich, J. V. "Analgesics" in *Burger's Medicinal Chemistry and Drug Discovery*, M. E. Wolff ed., John Wiley & Sons 1996, pages 321-44, the disclosures of which are incorporated herein by reference. In all but two of the foregoing compounds, there is a single phenolic OH that is to be replaced by G according to the present invention. In norbinaltorphimine and 361444-66-8, there are two phenolic OH's, either or both of which are replaced by G. Likewise, either or both amino nitrogens can be quaternized. Thus, the invention includes a process for modifying opioid ligands containing one or more hydroxy moieties and amino nitrogens comprising replacing one or more hydroxy groups with an amide group, or other polar neutral group, and quaternizing the amino nitrogen(s) and products produced by the process The compounds of the invention are useful for blocking or reversing non-CNS mediated side effects of opiates. One particular side effect that is ameliorated is the inhibition of gastrointestinal motility.

DEFINITIONS

Throughout this specification the terms and substituents retain their definitions.

Alkyl is intended to include linear, branched, or cyclic hydrocarbon structures and combinations thereof. A combination would be, for example, cyclopropylmethyl. Hydrocarbon refers to any substituent comprised of hydrogen and carbon as the only elemental constituents. Lower alkyl refers to alkyl groups of from 1 to 6 carbon atoms. Examples of lower alkyl groups include methyl, ethyl, propyl, isopropyl, cyclopropyl, butyl, s- and t-butyl, cyclobutyl and the like. Preferred alkyl groups are those of $C_{20}$ or below. Cycloalkyl is a subset of alkyl and includes cyclic hydrocarbon groups of from 3 to 8 or more carbon atoms. Examples of cycloalkyl groups include c-propyl, c-butyl, c-pentyl, norbornyl and the like.

Alkenyl refers to an unsaturated acyclic hydrocarbon radical in so much as it contains at least one double bond. Such radicals contain from 2 to 10 or more carbon atoms, preferably from 2 to 8 carbon atoms and more preferably 2 to 6 carbon atoms. Examples of suitable alkenyl radicals include propylenyl, buten-1-yl, isobutenyl, penten-1-yl, 2-methyl-buten-1-yl, 3-methylbuten-1-yl, hexen-1-yl, hepten-1-yl, and octen-1-yl, alkadienes and the like.

Alkynyl refers to an unsaturated acyclic hydrocarbon radical in so much as it contains at least one triple bond. Such radicals contain from 2 to 10 or more carbon atoms, preferably from 2 to 8 carbon atoms and more preferably 2 to 6 carbon atoms. Examples of suitable alkynyl radicals include propynyl, butyn-1-yl, pentyn-1-yl, butyn-2-yl, 3-methylbutyn-1-yl, hexyn-1-yl, heptyn-1-yl, and octyn-1-yl and the like.

Cycloalkyl or cycloalkenyl means an alicyclic radical in a ring (or fused ring system) with 3 to 10 carbon atoms, and preferably from 3 to 6 or more carbon atoms. Examples of suitable alicyclic radicals include cyclopropyl, cyclopropenyl, cyclobutyl, cyclopentyl, cyclohexyl, cyclohexenyl and the like.

Oxaalkyl refers to alkyl residues in which one or more carbons has been replaced by oxygen. Examples include methoxypropoxy, 3,6,9-trioxadecyl and the like.

Alkoxy or alkoxyl refers to groups of from 1 to 8 or more carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Acyl refers to formyl and to groups of 1, 2, 3, 4, 5, 6, 7 and 8 or more carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur, or two hydrogens may be replaced or interrupted by oxygen, as long as the point of attachment to the parent remains at the carbonyl. Examples include acetyl, benzoyl, propionyl, isobutyryl, t-butoxycarbonyl, benzyloxycarbonyl and the like. Loweracyl refers to groups containing one to six or more, e.g., four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, thiazole, furan, benzimidazole, quinoline, isoquinoline, quinoxaline, pyrimidine, pyrazine, tetrazole and pyrazole.

Arylalkyl or aralkyl means an alkyl residue attached to an aryl ring. Examples are benzyl, phenethyl and the like. Heteroarylalkyl means an alkyl residue attached to a heteroaryl ring. Examples include, e.g., pyridinylmethyl, pyrimidinylethyl and the like.

Heterocycle means a cycloalkyl or aryl residue in which one to two or more of the carbons is replaced by a heteroatom such as oxygen, nitrogen or sulfur. Heteroaryls form a subset of heterocycles. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like.

Substituted alkyl, aryl, cycloalkyl, heterocyclyl etc. refer to alkyl, aryl, cycloalkyl, or heterocyclyl wherein up to three or more H atoms in each residue are replaced with, for example, halogen, haloalkyl, alkyl, acyl, alkoxyalkyl, hydroxyloweralkyl, phenyl, heteroaryl, benzenesulfonyl, hydroxy, loweralkoxy, haloalkoxy, carboxy, carboalkoxy (also referred to as alkoxycarbonyl), alkoxycarbonylamino, carboxamido (also referred to as alkylaminocarbonyl), cyano, carbonyl (also referred to as oxo), acetoxy, nitro, amino, alkylamino, dialkylamino, mercapto, alkylthio, sulfoxide, sulfone, sulfonylamino, acylamino, amidino, aryl, benzyl, heterocyclyl, phenoxy, benzyloxy, heteroaryloxy, hydroxyimino, alkoxyimino, oxaalkyl, aminosulfonyl, trityl, amidino, guanidino, ureido, and benzyloxy.

The term "pharmaceutically acceptable salt" refers to salts whose counter ion derives from pharmaceutically acceptable non-toxic acids and bases. Suitable pharmaceutically acceptable base addition salts for the compounds of the present invention include inorganic acids, organic acids and, since the compounds possess a quaternary ammonium radical, water (which formally furnishes the hydroxide anion). Examples of counterions include hydroxide, acetate, benzenesulfonate (besylate), benzoate, bicarbonate, bisulfate, carbonate, camphorsulfonate, citrate, ethanesulfonate, fumarate, gluconate, glutamate, glycolate, bromide, chloride, isethionate, lactate, maleate, malate, mandelate, methanesulfonate, mucate, nitrate, pamoate, pantothenate, phosphate, succinate, sulfate, tartrate, trifluoroacetate, p-toluenesulfonate, acetamidobenzoate, adipate, alginate, aminosalicylate, anhydromethylenecitrate, ascorbate, aspartate, calcium edetate, camphorate, camsylate, caprate, caproate, caprylate, cinnamate, cyclamate, dichloroacetate, edetate (EDTA), edisylate, embonate, estolate, esylate, fluoride, formate, gentisate, gluceptate, glucuronate, glycerophosphate, glycolate, glycollylarsanilate, hexylresorcinate, hippurate, hydroxynaphthoate, iodide, lactobionate, malonate, mesylate, napadisylate, napsylate, nicotinate, oleate, orotate, oxalate, oxoglutarate, palmitate, pectinate, pectinate polymer, phenylethylbarbiturate, picrate, pidolate, propionate, rhodanide, salicylate, sebacate, stearate, tannate, theoclate, tosylate, and the like.

When the compounds contain an acidic residue, the compounds can exist as zwitterions. Additionally suitable pharmaceutically acceptable base addition salts for the compounds of the present invention include ammonium, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Other base addition salts includes those made from: arecoline, arginine, barium, benethamine, benzathine, betaine, bismuth, clemizole, copper, deanol, diethylamine, diethylaminoethanol, epolamine, ethylenediamine, ferric, ferrous, glucamine, glucosamine, histidine, hydrabamine, imidazole, isopropylamine, manganic, manganous, methylglucamine, morpholine, morpholineethanol, n-ethylmorpholine, n-ethylpiperidine, piperazine, piperidine, polyamine resins, purines, theobromine, triethylamine, trimethylamine, tripropylamine, trolamine, and tromethamine.

The compounds of the invention are salts and will therefore have counterions. The counterions of the invention are pharmaceutically acceptable counterions. Pharmaceutically acceptable counterions include, for example, halides, sulfates, phosphates, nitrates, and anionic organic compounds. Halides include iodide, bromide, chloride and combinations thereof.

A person skilled in the art would understand that if a compound of the invention is prepared as one salt (e.g. an iodide salt) it can be readily converted to another salt (e.g. a bromide salt) by passing it through an anion exchange column.

Virtually all of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as their racemic and optically pure forms. In general it has been found that the levo isomer of morphinans and benzomorphans is the more potent antinociceptive agent, while the dextro isomer may be useful as an antitussive or antispasmodic agent. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The configuration of the newly created chiral center at nitrogen is arbitrarily depicted. In some cases the depiction may suggest R and in some it may suggest S. These depictions should not be taken as indicating that the absolute stereochemistry has been determined. It will be appreciated that the alkylation of the nitrogen to form a chiral molecule (as most are) is likely to prefer one isomer. In some cases in which we have examined the chirality, the R configuration predominates at N, and the diastereomer that is recovered upon recrystallization has the R configuration at N. One assumes that some finite amount of the opposite configuration can also be formed and may remain in the mother liquors. If it were desired, this isomer and/or any racemic or diastereoisomeric mixture can be recovered or produced by techniques well known to those of skill in the art. Further, several chiral carbons are possible as well. Unless expressly otherwise stated in the claim, the claims are intended to encompass both or all isomers and mixtures, irrespective of whether the claim employs a formula which depicts the chirality of a center.

ABBREVIATIONS

A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations", is incorporated herein by reference. The following abbreviations and terms have the indicated meanings throughout:
Ac=acetyl
BNB=4-bromomethyl-3-nitrobenzoic acid
Boc=t-butyloxy carbonyl
Bu=butyl
c-=cyclo
CHO=Chinese hamster ovary
DAMGO=Tyr-ala-Gly-NMePhe-NHCH$_2$OH
DBU=diazabicyclo[5.4.0]undec-7-ene
DCM=dichloromethane=methylene chloride=CH$_2$Cl$_2$
DEAD=diethyl azodicarboxylate
DIC=diisopropylcarbodiimide
DIEA=N,N-diisopropylethyl amine
DMAP=4-N,N-dimethylaminopyridine
DMF=N,N-dimethylformamide
DMSO=dimethyl sulfoxide
DOR=delta opioid receptor
DPPF=1,1'-bis(diphenylphosphino)ferrocene
DVB=1,4-divinylbenzene
EC$_{50}$=concentration of a drug that produces 50% effect
EEDQ=2-ethoxy-1-ethoxycarbonyl-1,2-dihydroquinoline
EGTA=ethylene glycol tetraacetic acid
E$_{max}$=maximum effect (of a drug)
Fmoc=9-fluorenylmethoxycarbonyl
GC=gas chromatography
GI=gastrointestinal
HATU=O-(7-Azabenzotriazol-1-yl)-1,1,3,3-tetramethyluronium hexafluorophosphate
HOAc=acetic acid
HOBt=hydroxybenzotriazole
IC$_{50}$=concentration of a drug that produces 50% inhibition
I$_{max}$=maximum inhibition (of a drug)
IP=intraperitoneal
IV=intravenous
KOR=kappa opioid receptor
Me=methyl
mesyl=methanesulfonyl
mNTX=methyl-naltrexone
MOR=mu opioid receptor
MRL=maximum response latency
MTBE=methyl t-butyl ether
NMO=N-methylmorpholine oxide
NOESY=Nuclear Overhauser Enhancement Spectroscopy
PD=pharmacodynamic(s)
PEG=polyethylene glycol
PGE$_2$=prostaglandin E$_2$
Ph=phenyl
PhOH=phenol
PfP=pentafluorophenol
PK=pharmacokinetic(s)
PO=oral administration
PPTS=pyridinium p-toluenesulfonate
PyBroP=bromo-tris-pyrrolidino-phosphonium hexafluorophosphate
rt=room temperature sat'd=saturated
s-=secondary
SC=subcutaneous
t-=tertiary
TBDMS=t-butyldimethylsilyl
TFA=trifluoroacetic acid
THF=tetrahydrofuran
TMOF=trimethyl orthoformate
TMS=trimethylsilyl
tosyl=p-toluenesulfonyl
Trt=triphenylmethyl
U50,488=κ agonist It may happen that residues in the substrate of interest require protection and deprotection during the conversion of the phenol to the desired biostere or the quaternization. Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is below, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

Preferred compounds of the invention were prepared by quaternizing a tertiary amine precursor with an appropriate alkylating agent, for example, methyl halide or sulfate:

Scheme 1
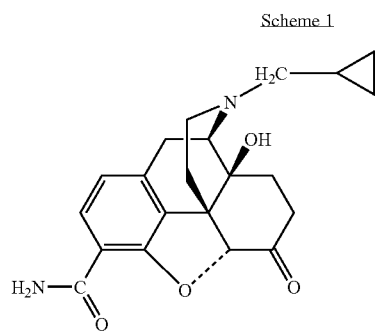
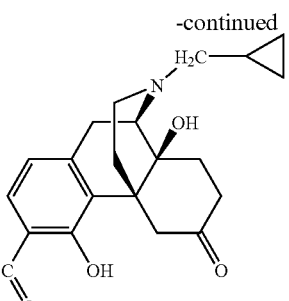
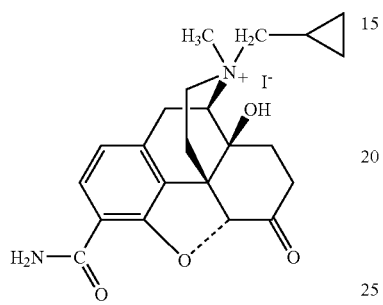
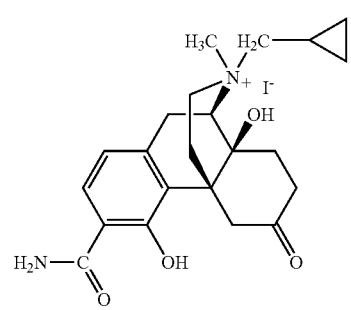
Starting compounds for preparing compounds of the invention may be synthesized by one of the routes described in U.S. Pat. Nos. 6,784,187 and 7,057,035, and in U.S. Patent Application Publication No.: US 2007/0021457. For example:
Scheme 2
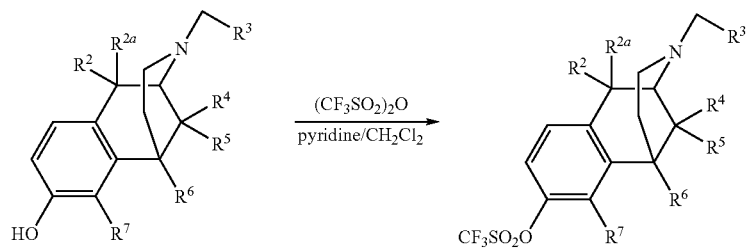
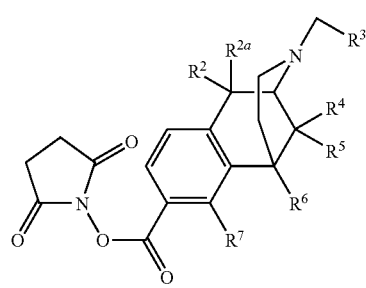

23 24
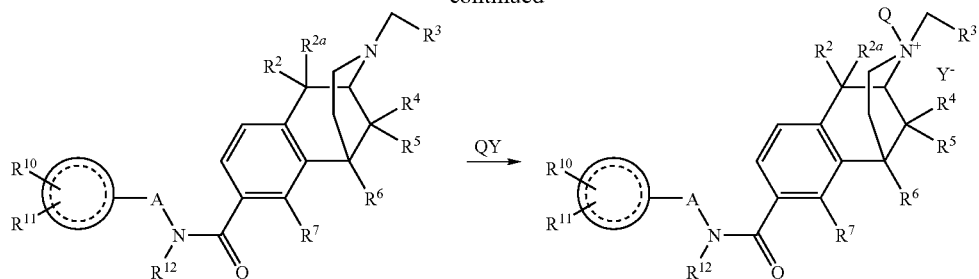
Scheme 3
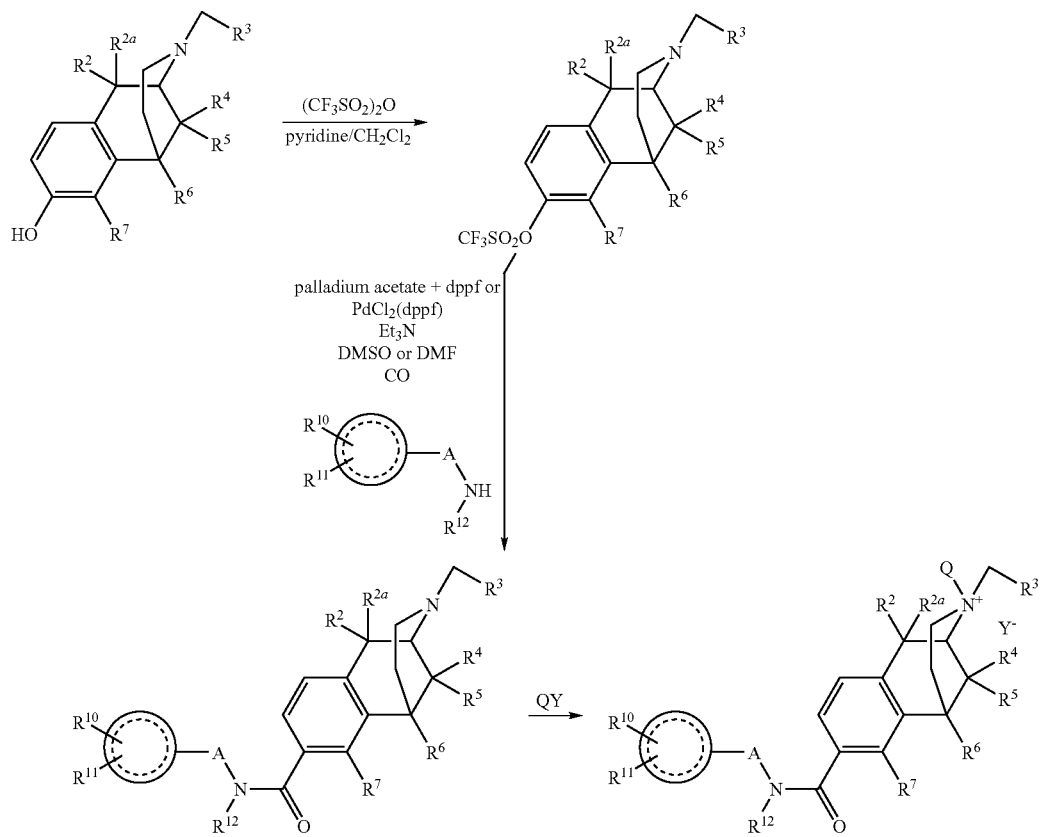
Scheme 4
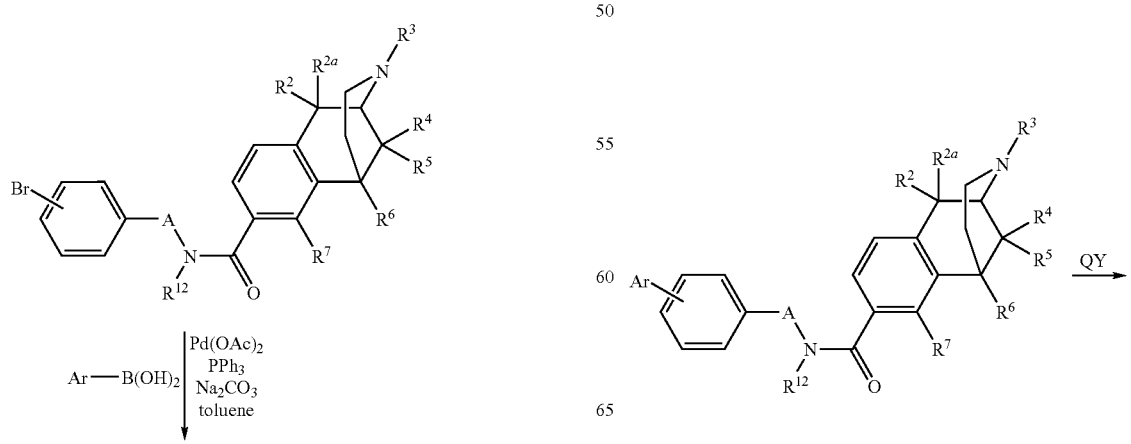

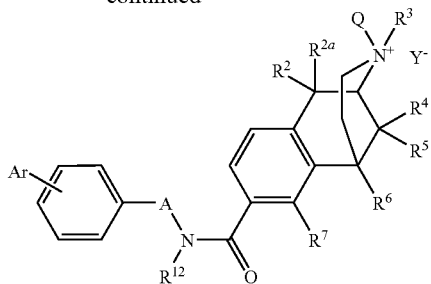

The N-hydroxysuccinimide ester intermediates (3) shown in Scheme 2 may be prepared by the processes of U.S. Pat. No. 7,057,035, which is incorporated herein by reference. The N-hydroxysuccinimide ester is then reacted with the appropriate arylalkylamine (4) as described below. An alternative, employing direct carbonylation/amidation is shown in Scheme 3. Many diaryl compounds can be prepared by Suzuki coupling, shown in Scheme 4.

Experimental Section

In vitro and in vivo studies have been conducted with example compounds. In vitro define the receptor binding and functional activity of these molecules. In vivo studies were conducted to demonstrate the relative peripheral to central nervous system activity. For one example (Compound 6) pharmacokinetics studies were conducted to illustrate the ability inhibit morphine's blockade of PGE$_2$-induced diarrhea.

Opioid Receptor Binding Assays

We have examined opioid receptor binding affinities of compounds in this series. Binding assays used to screen compounds are similar to those previously reported by Neumeyer et al., Design and Synthesis of Novel Dimeric Morphinan Ligands for κ and μ Opioid Receptors. J. Med. Chem. 2003, 46, 5162. Membrane protein from CHO cells that stably expressed one type of the human opioid receptor were incubated with 12 different concentrations of the compound in the presence of either 1 nM [$^3$H]U69,593 (κ), 0.25 nM [$^3$H] DAMGO (μ) or 0.2 nM [$^3$H]naltrindole (δ) in a final volume of 1 mL of 50 mM Tris-HCl, pH 7.5 at 25° C. Incubation times of 60 min were used for [$^3$H]U69,593 and [$^3$H]DAMGO. Because of a slower association of [$^3$H]naltrindole with the receptor, a 3 h incubation was used with this radioligand. Samples incubated with [$^3$H]naltrindole also contained 10 mM MgCl$_2$ and 0.5 mM phenylmethylsulfonyl fluoride. Nonspecific binding was measured by inclusion of 10 μM naloxone. The binding was terminated by filtering the samples through Schleicher & Schuell No. 32 glass fiber filters using a Brandel 48-well cell harvester. The filters were subsequently washed three times with 3 mL of cold 50 mM Tris-HCl, pH 7.5, and were counted in 2 mL Ecoscint A scintillation fluid. For [$^3$H]naltrindole and [$^3$H]U69,593 binding, the filters were soaked in 0.1% polyethylenimine for at least 60 min before use. IC$_{50}$ values were calculated by least squares fit to a logarithm-probit analysis. K$_i$ values of unlabeled compounds were calculated from the equation K$_i$=(IC$_{50}$)/1+S where S=(concentration of radioligand)/(K$_d$ of radioligand). Data are the mean±SEM from at least three experiments performed in triplicate.

[35S]GTPγS Binding Assays

The assays that were used to screen compounds are similar to those previously reported by Wentland et al., "Redefining the structure-activity relationships of 2,6-methano-3-benzazocines. Part 4. Opioid receptor binding properties of 8-[N-(4'-phenyl)-phenethyl)carboxamido] analogues of cyclazocine and EKC" J. Med. Chem. 2006, 49, 5635. In a final volume of 0.5 mL, 12 different concentrations of each test compound were incubated with 15 μg (κ), 10 μg (δ) or 7.5 μg (μ) of CHO cell membranes that stably expressed either the human κ or μ opioid receptor. The assay buffer consisted of 50 mM Tris-HCl, pH 7.4, 3 mM MgCl$_2$, 0.2 mM EGTA, 3 μM GDP, and 100 mM NaCl. The final concentration of [35S] GTPγS was 0.080 nM. Nonspecific binding was measured by inclusion of 10 μM GTPγS. Binding was initiated by the addition of the membranes. After an incubation of 60 min at 30° C., the samples were filtered through Schleicher & Schuell No. 32 glass fiber filters. The filters were washed three times with cold 50 mM Tris-HCl, pH 7.5, and were counted in 2 mL of Ecoscint scintillation fluid. Data are the mean Emax and EC$_{50}$ values±S.E.M. from at least three separate experiments, performed in triplicate. For calculation of the E$_{max}$ values, the basal [35S]GTPγS binding was set at 0%. To determine antagonist activity of a compound at the μ opioid receptors, CHO membranes expressing the μ opioid receptor, were incubated with 12 different concentrations of the compound in the presence of 200 nM of the μ agonist DAMGO. To determine antagonist activity of a compound at the κ opioid receptors, CHO membranes expressing the κ opioid receptor, were incubated with the compound in the presence of 100 nM of the κ agonist U50,488. To determine if a compound was an antagonist at δ receptors, CHO membranes expressing the δ receptor were incubated with 12 different concentrations of the test compound in the presence of 10 nM of the δ-selective agonist SNC 80.

Antinociceptive activity of the opiate whose side effect is to be ameliorated is evaluated by the method described in Jiang et al. [J. Pharmacol. Exp. Ther. 264, 1021-1027 (1993), page 1022].

The effect on G.I. motility is evaluated by the method described by Gmerek, Debra E.; Cowan, Alan; Woods, James H. "Independent central and peripheral mediation of morphine-induced inhibition of gastrointestinal transit in rats." Journal of Pharmacology and Experimental Therapeutics (1986), 236(1), 8-13.

PGE$_2$ Model of Gut Motility

To assess the effects of novel, peripherally acting opioid antagonists, we used a PGE$_2$ (a prostaglandin) model of gut motility. PGE$_2$ induces diarrhea within 15 minutes of an intraperitoneal (IP) injection (0.1 mg/kg) in mice. Pretreatment (30 minutes) with morphine (1 mg/kg) blocks this effect. We tested the ability of peripherally acting opioid antagonists to inhibit morphine's blockade of diarrhea.

Each opioid antagonist was tested with morphine to establish a dose-response antagonism of morphine's ability to block PGE$_2$-induced diarrhea. Mice (n=10/group) were given either an IP injection or oral (PO) administration (via gavage) of a novel opioid antagonist (0-3 mg/kg, IP; 0-30 mg/kg, PO) and placed in a Plexiglas pie cage (Braintree Scientific, Braintree, Mass.). Each pie cage holds up to 10 mice and is 21.5 cm in diameter and 7.5 cm in height. Individual chambers are 5 cm (base) and 9 cm (length). For the initial studies, morphine (1 mg/kg, IP) was administered 15 minutes after administration of the novel opioid antagonist and mice were returned to the pie cage. 30 minutes later mice were treated with PGE$_2$ (0.1 mg/kg, IP) and again returned to the pie cage. During the final observation, the presence or absence of diarrhea was recorded 15 minutes following PGE$_2$ administration. Mice were only tested once. Saline-saline (10 mL/kg, IP) and saline-morphine were the positive control groups and all results were compared to the saline-morphine treatment group. Data represent the percent of mice with PGE$_2$-induced diarrhea at the time of the final observation.

Tail Flick Antinociception Test

Antinociception to acute thermal stimuli was assessed using a commercially available tail flick apparatus (Columbus Instruments, Columbus, Ohio). The tail flick test is purported to be primarily a peripheral reflexive response assay. In this standard model, mice are gently restrained and their tail is placed over a thermal beam. Once the beam is turned on (instant on; 9.3 watts), the time required to reflexively flick the tail is recorded. The maximum response latency (MRL) was set to 10 seconds to avoid potential thermal injury associated with longer exposure times. If there is no response after 10 seconds, mice are removed and the maximum response latency (MRL; 10 s) is recorded.

Morphine (15 mg/kg, IP, administered 45 minutes prior to testing) produces a MRL or a near MRL. Each opioid antagonist was tested with morphine to establish a dose-response antagonism of morphine-induced antinociception in the tail flick test. Mice (n=10/group) were first tested in the tail flick test to determine a baseline response. Mice were excluded from the study if they had a baseline response time of greater than 10 seconds. The mice were administered different doses of an opioid antagonist (IP or PO, 60 minutes prior to testing in the tail flick test). Fifteen minutes later, they were injected with morphine (IP, 15 mg/kg 45 minutes prior to testing in the tail flick test). All results are compared to the saline-morphine treatment group mean response latency.

Hot Plate Antinociception Test

Antinociception to acute thermal stimuli was assessed using a commercially available hot plate apparatus (Columbus Instruments, Columbus, Ohio). The hot plate test is purported to be a supraspinal assay of nociception. The hot plate procedure involves placing each mouse on a heated surface and activating a timer. Mice were placed individually on a hot plate (25.4 cm×25.4 cm surrounded by an acrylic box to prevent the animal from escaping); surface temperature=55° C.) and the response latency to lick either hind paw was recorded. The maximum response latency (MRL) was set to 60 seconds to avoid potential thermal injury associated with longer exposure times. The mouse is removed from the heated surface when it either licks a hind paw in response to the heat or after 60 seconds has elapsed. The latency to respond is recorded and the mouse is returned to its home cage.

Morphine (15 mg/kg, IP, administered 45 minutes prior to testing) produces a MRL or near MRL. Each opioid antagonist was tested with morphine to establish a dose-response antagonism of morphine-induced antinociception. Mice (n=10/group) were first tested to determine a baseline response. Mice were excluded from the study if they had a baseline response time of greater than 30 seconds. Mice were then administered different doses of an opioid antagonist (IP or PO, 60 minutes prior to testing on the hot plate test). Fifteen minutes later, they were injected with morphine (IP, 15 mg/kg 45 minutes prior to testing on the hot plate test). All results are compared to the saline-morphine treatment group mean response latency.

Methods for PK evaluation of Compound 6 (see below). Animals were dosed with the example compound and blood samples were collected for 2 hours using the following method. Rats were briefly anesthetized with 1-2% isoflurane and blood samples (approximately 250 mL of whole blood) from a lateral tail vein were collected into tubes containing EDTA. The tubes were centrifuged at 10K×g for 2 minutes to separate plasma. Plasma was pipetted into microcentrifuge vials and stored at −80° C. until plasma levels were determined by liquid chromatography-mass spectrometry/mass spectrometry (LC-MS/MS) (modification of Baranczewski et al., 2006). The lower limit of quantitation (LOQ) for these studies was 1.0 ng/mL and the coefficient of variation for the assay was <4.4%. The mean concentration of the example compound in plasma was calculated for each time point. If a value was less than the LOQ, it was given a value of zero.

A bioanalytical assay was developed and qualified for measurement of the example compound in rat plasma. The procedure involved analysis of an acetonitrile precipitated protein extract of rat plasma by high performance liquid chromatography coupled with PE/Sciex API 2000 mass spectrometer (LC-MS/MS). Assay standards and controls were prepared by spiking blank plasma with naltrexone (Sigma Chemical, St. Louis, Mo.) in order to achieve concentrations of 100 ng/mL for standards which were diluted further during each sample analysis and 80 ng/mL, 40 ng/mL, and 8 ng/mL for assay controls. Extraction was performed by transferring 100 mL of each standard, sample and control into microcentrifuge tubes containing 10 mL of internal standard (1 mg/mL hydrocodone in acetonitrile) and 10 mL of 10 mM sodium bicarbonate buffer. Then 250 mL of acetonitrile was used to precipitate protein, the clear supernatant was removed, concentrated to dryness, and reconstituted with 100 mL of mobile phase buffer mixture. For analysis, 5 mL of the reconstituted extract was injected onto LC-MS/MS system. The high performance liquid chromatography was performed isocratically at ambient temperature using a Waters C18 3.5m column (XBridge, 2.1×50 mm i.d., Milford, Mass.) The mobile phase consisted of 10 mM ammonium acetate, 0.1% ammonium hydroxide buffer (pH 9.0+0.5) and acetonitrile (45:55, v/v). The flow rate was 0.350 mL/min. An AP12000 (Applied Biosystems, Forest City, Calif.) triple quadrupole was equipped with Turbolon Spray source. Peak areas of the m/z 342→324 for naltrexone product ion and m/z 300→199 for product ion of the internal standard were measured using positive ion mode. Ion Spray voltage was set to 4500V, nebulizer gas at 25 psi, heater gas at 55 psi, and probe temperature at 350° C. Data analysis was performed using Analyst software (Applied Biosystems, version 1.2). The standard curves were plotted as the peak area ratio (analyte/IS) vs. analyte nominal concentration with a weighting factor of 1/y. Standard curves were linear in the range from 1 ng/mL to 100 ng/mL with a coefficient of determination (r2)>0.990 (n=10). The LOQ for naltrexone was defined as 1 ng/mL. The intra-day accuracy and precision were evaluated by analysis of each 80 ng/mL, 40 ng/mL, and 8 ng/mL assay control (n=5 at each concentration) on the same day. Accuracy was calculated as a percentage ratio of measured concentration to nominal concentration and precision was expressed as the coefficient of variation. The accuracy was 86%, 100%, and 103%, and precision 3.6%, 2.9% and 1.9% respectively. Intra-day accuracy and precision were evaluated for each 80 ng/mL, 40 ng/mL, and 8 ng/mL assay control over 10 different runs (n=26 for each control sample). Accuracy was 103%, 103%, and 115%, and precision was 10.1%, 14.1%, and 19.1% respectively. Freeze and thaw stability was determined by analyzing assay control samples at the concentrations of 80 ng/mL, 40 ng/mL, and 8 ng/mL following three cycles of freezing at −69° C. and thawing. Stability was expressed as a percentage ratio of measured concentration to the nominal. The % recovery was 97% for cycle 1, 100% for cycle 2, and 98% for cycle 3.

Experimental Results

In the text, tables and graphs, compounds (cmpds) 2, 4, 6, 8, 10, 12 and 14 refer to the following compounds:

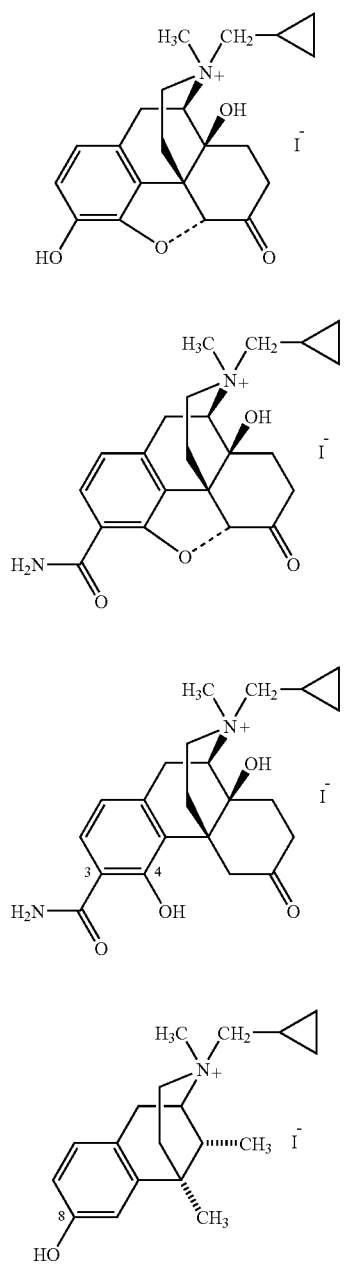
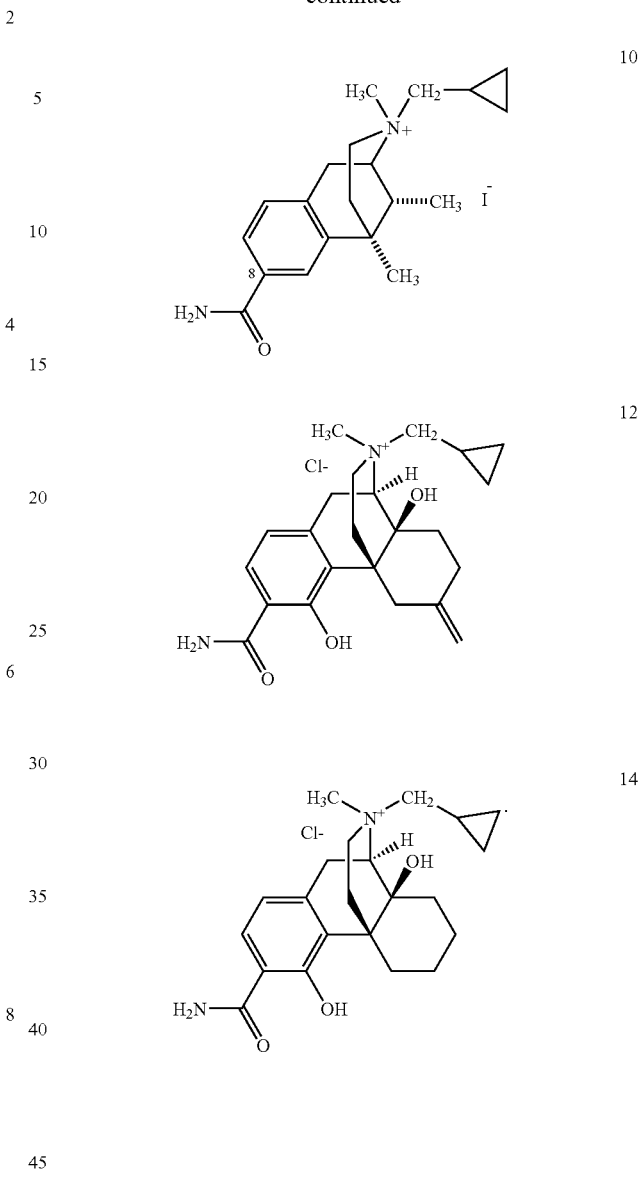

In Table 1, lower numbers indicate that a compound is more potent at that receptor. For instance, Compound 8 has a high affinity for the μ receptor ($K_i$=0.91 nM), but a much lower affinity for the δ receptor ($\kappa_i$=550 nM).

TABLE 1

| Binding Affinity--Comparison with Naltrexone | | | | |
|---|---|---|---|---|
| Compound | [³H]DAMGO (μ) $K_i$ nM | [³H]Naltrindole (δ) $K_i$ nM | [³H]U69,593 (κ) $K_i$ nM | K:μ | K:δ |
| Naltrexone | 0.11 ± 0.006 | 60 ± 3.2 | 0.19 ± 0.005 | 0.6 | 3320 |
| 2 | 2.0 ± 0.27 | 900 ± 36 | 6.3 ± 0.46 | 0.32 | 143 |
| 4 | 37 ± 1/6 | 31% inh. @ 10 μm | 210 ± 22 | 0.18 | 143 |
| 6 | 1.3 ± 0.13 | 280 ± 21 | 7.7 ± 0.90 | 0.17 | — |
| 8 | 0.91 ± 0.092 | 550 ± 36 | 5.8 ± 0.59 | 0.2 | 95 |
| 10 | 1.4 ± 0.19 | 360 ± 6.5 | 17 ± 1.2 | 0.082 | 21 |

In Table 2, the IC$_{50}$ (indicating antagonist activity) of Compound 6 is 52 nM at the µ receptor and 7800 at the κ receptor. This indicates that Compound 6 has greater inhibitory activity at µ than for the κ opioid receptor. Compound 6 did not display any agonist properties at either the µ or the κ opioid receptor.

TABLE 2

| | GTPγS Functional Assay Results | | | | | | | |
|---|---|---|---|---|---|---|---|---|
| | Mu | | | | Kappa | | | |
| | Cmpd. Alone (Mean ± S.E) | | With DAMGO (Mean ± S.E) | | Cmpd. Alone (Mean ± S.E) | | With U50,488 (Mean ± S.E) | |
| cmpd | EC50 (nM) | Emax (%) | IC50 (nM) | Imax (%) | EC50 (nM) | Emax (%) | IC50 (nM) | Imax (%) |
| 6 | Not applicable | −0.28 ± 0.39 | 52 ± 20 | 96 ± 1.2 | Not applicable | 3.0 ± 2.6 | 7800 ± 530 | 88 ± 1.4 |

In vivo Results for Compound 6. Compound 6 was evaluated in mice using the PGE2 model of gut motility, the tail flick and hot plate models of antinociception using two routes of drug administration (intraperitoneal (IP) and oral (PO)). The Oral and subcutaneous bioavailability of Compound 6 was also studied in rats. This combination of methods allows the identification of compounds with a preferred combination of properties—orally active, yet with relatively poor CNS activity due to limited penetration of the blood brain barrier and/or low absorption from the gastrointestinal tract.

Effects of Compound 6 on PGE$_2$-induced Diarrhea in Mice. Compound 6 was administered to mice using both the IP and PO routes of administration (FIG. 1). Each route of administration resulted in a dose-dependent reversal of the effects of morphine (note: in this model morphine inhibits PGE$_2$-induced diarrhea). Importantly very good activity in blocking PGE$_2$-induced diarrhea was observed at doses of 1-10 mg/kg for both routes of administration.

Figure 2:
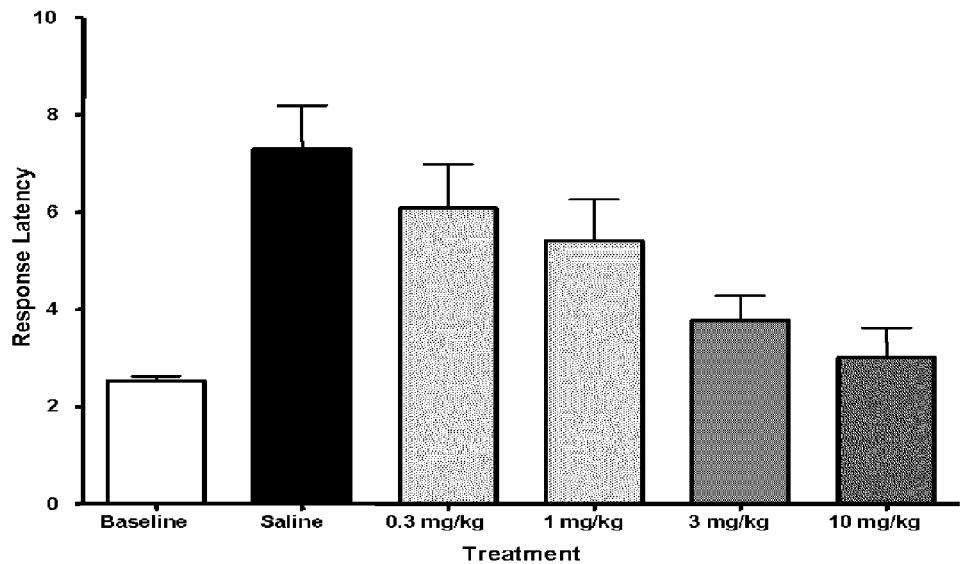
FIG. 2 is a graph of response latency (in seconds) vs. dose showing the effects on morphine-induced analgesia of Compound 6 in the tail flick test (intraperitoneal and oral administration).
Figure 2:
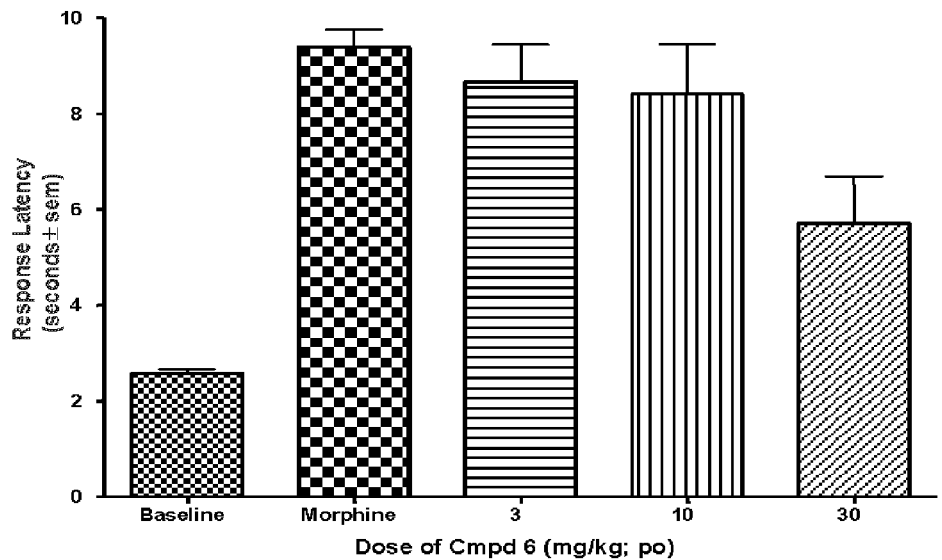

Effects of Compound 6 in the Mouse Tail Flick Antinociception Test. The tail flick assay is primarily a peripheral reflect response. Compound 6 was moderately effective when given by the IP route in blocking the analgesic effects of morphine. However in this assay and in contrast to the PGE$_2$ model, the oral administration of Compound 6 was much less effective in blocking the effects of morphine. A dose of 10 mg/kg of Compound 6 did not affect the response to morphine and at maximum dose evaluated (30 mg/kg) the effect of morphine was only partially reverse (FIG. 2). The differences observed between the tail-flick and PGE$_2$ are desired outcomes, indicating a more peripheral and gut selective action of Compound 6.

Figure 3:
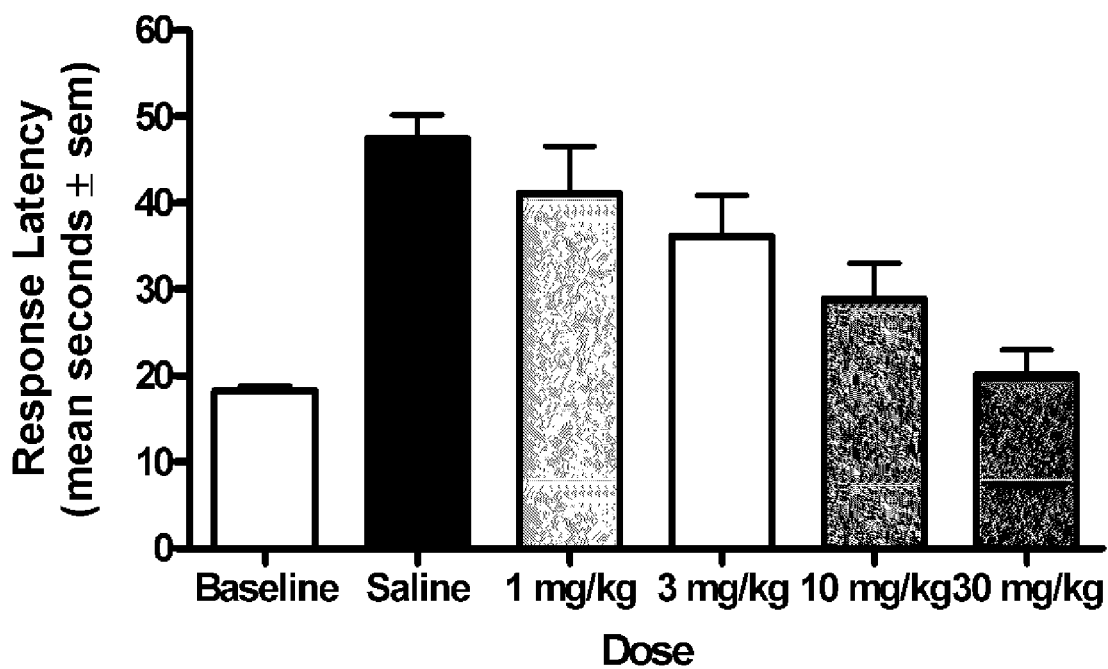
FIG. 3 is a graph of response latency (in seconds) vs. dose showing the effects on morphine-induced analgesia of Compound 6 in the hot plate test (intraperitoneal and oral administration).

Effects of Compound 6 in the Mouse Hot Plate Antinociception Test. In contrast to the tail flick assay, the hot plate is believed to reflect a supraspinal assay of nociception. Compound 6 was marginally effective when given by the IP route in blocking the analgesic effects of morphine. (FIG. 3). While there was a significant dose response, even at doses of 3 mg/kg, there was only about a 20-25% change from the baseline morphine response. When given orally at doses up to 30 mg/kg Compound 6 had no effect on the response to morphine. This is a very positive result indicating that oral administration of Compound 6 would have the ability to reverse peripheral adverse actions of opiates without affecting their spinal cord and central therapeutic actions.

Figure 4:
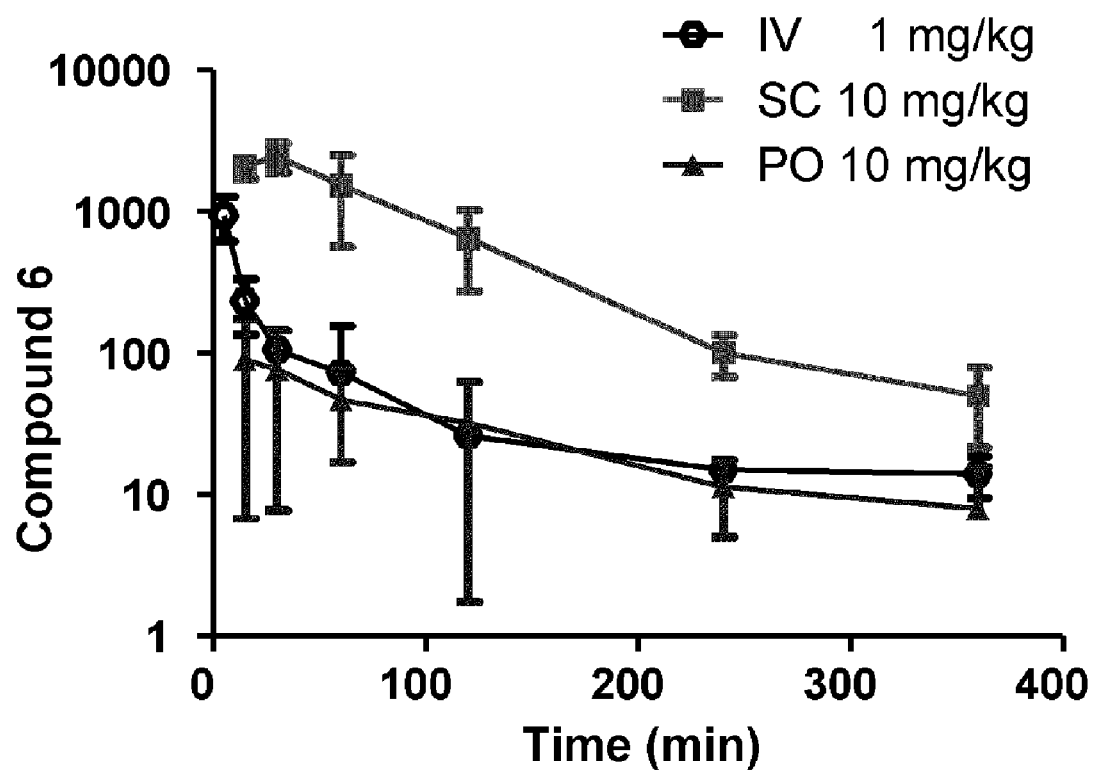
FIG. 4 is a graph of dose vs. time in minutes showing pharmacokinetic results of Compound 6 in various administration forms.
Figure 5:
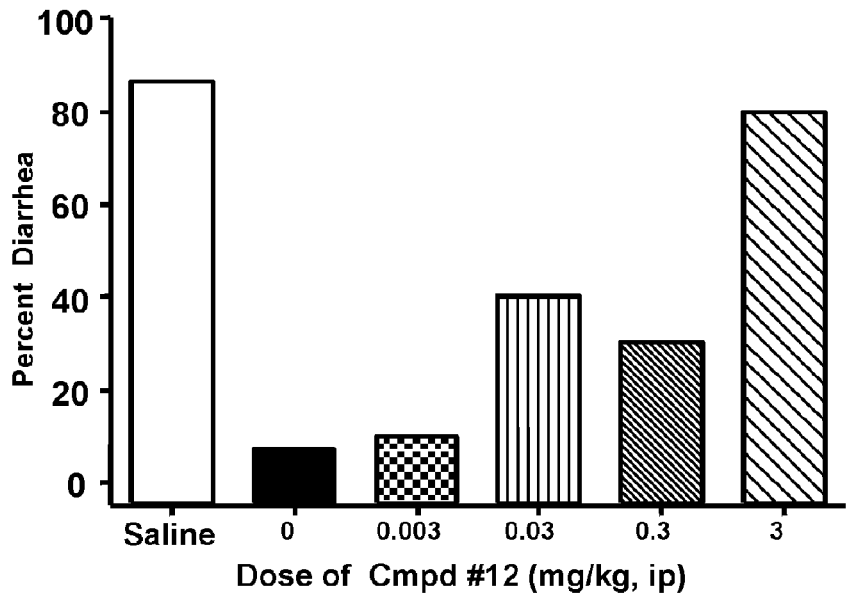
FIG. 5 is a graph of percent diarrhea vs. dose showing the inhibition of morphine blockade of $PGE_2$-induced diarrhea for mice treated with Compound 12 (intraperitoneal and oral administration).
Figure 5:
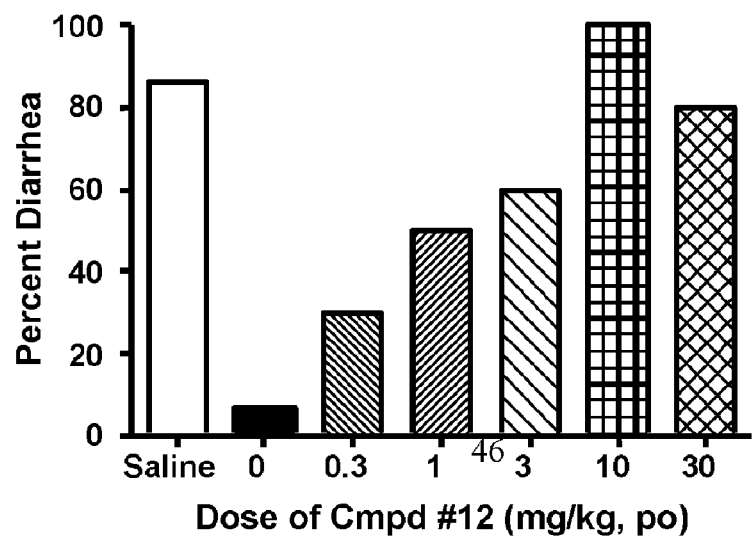
Figure 6:
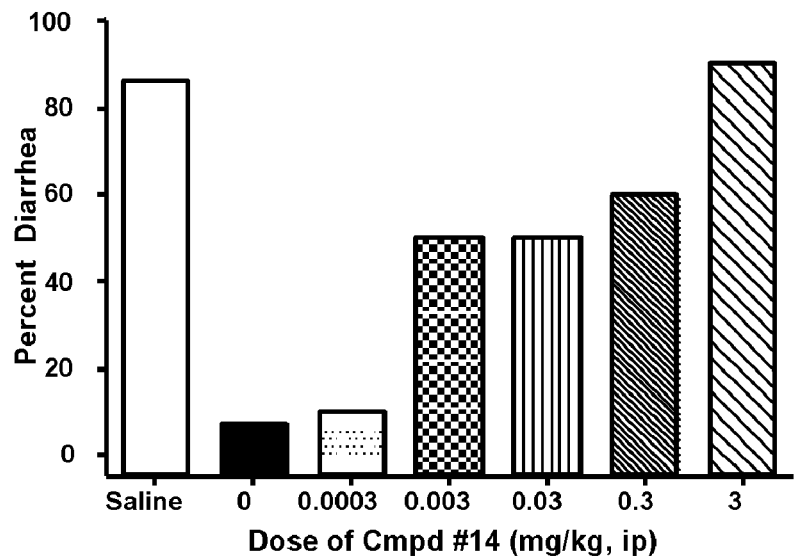
FIG. 6 is a graph of percent diarrhea vs. dose showing the inhibition of morphine blockade of $PGE_2$-induced diarrhea for mice treated with Compound 14 (intraperitoneal and oral administration).
Figure 6:
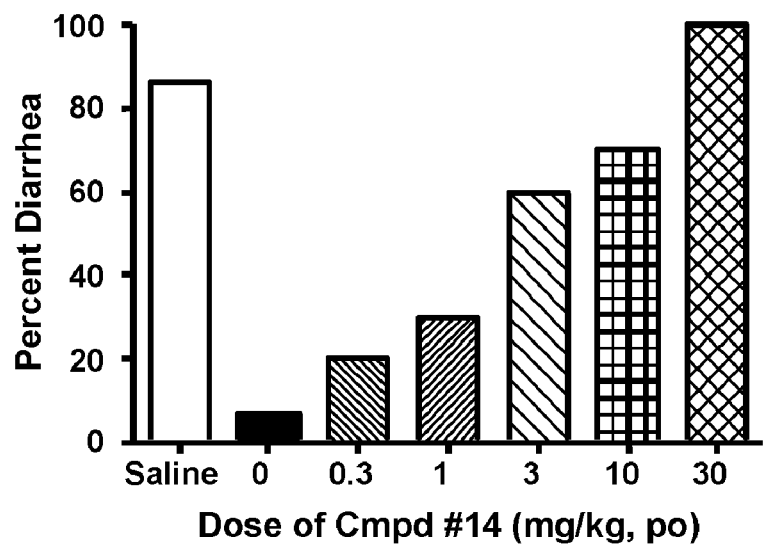
Figure 7:
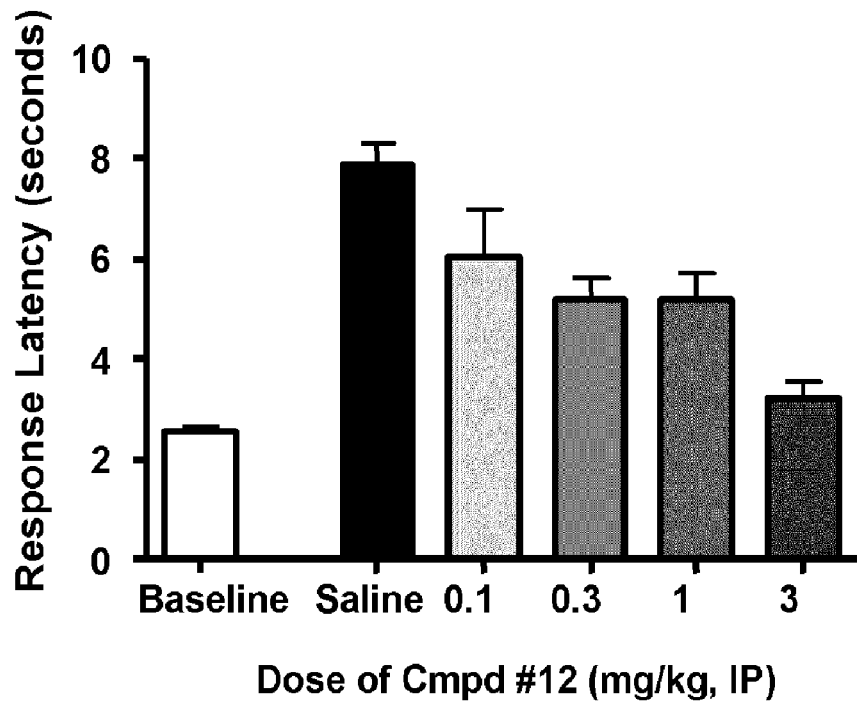
FIG. 7 is a graph of response latency (in seconds) vs. dose showing the effects on morphine-induced analgesia of Compound 12 in the tail flick test (intraperitoneal and oral administration).
Figure 7:
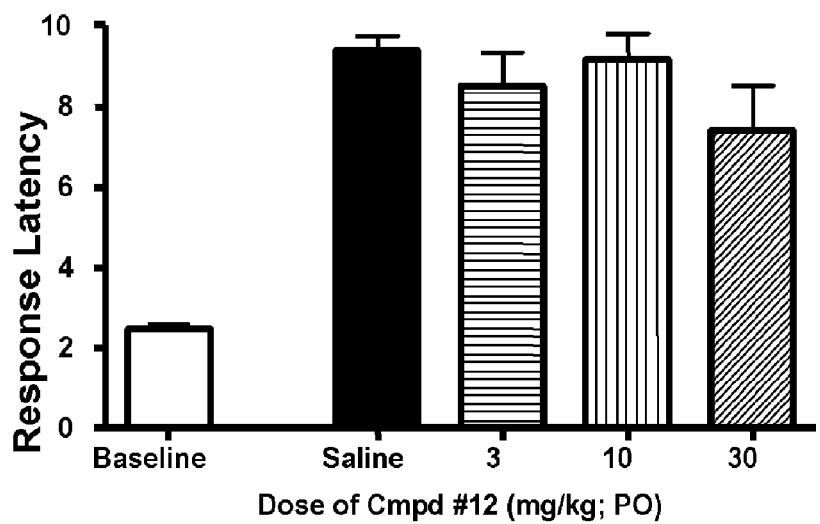
Figure 8:
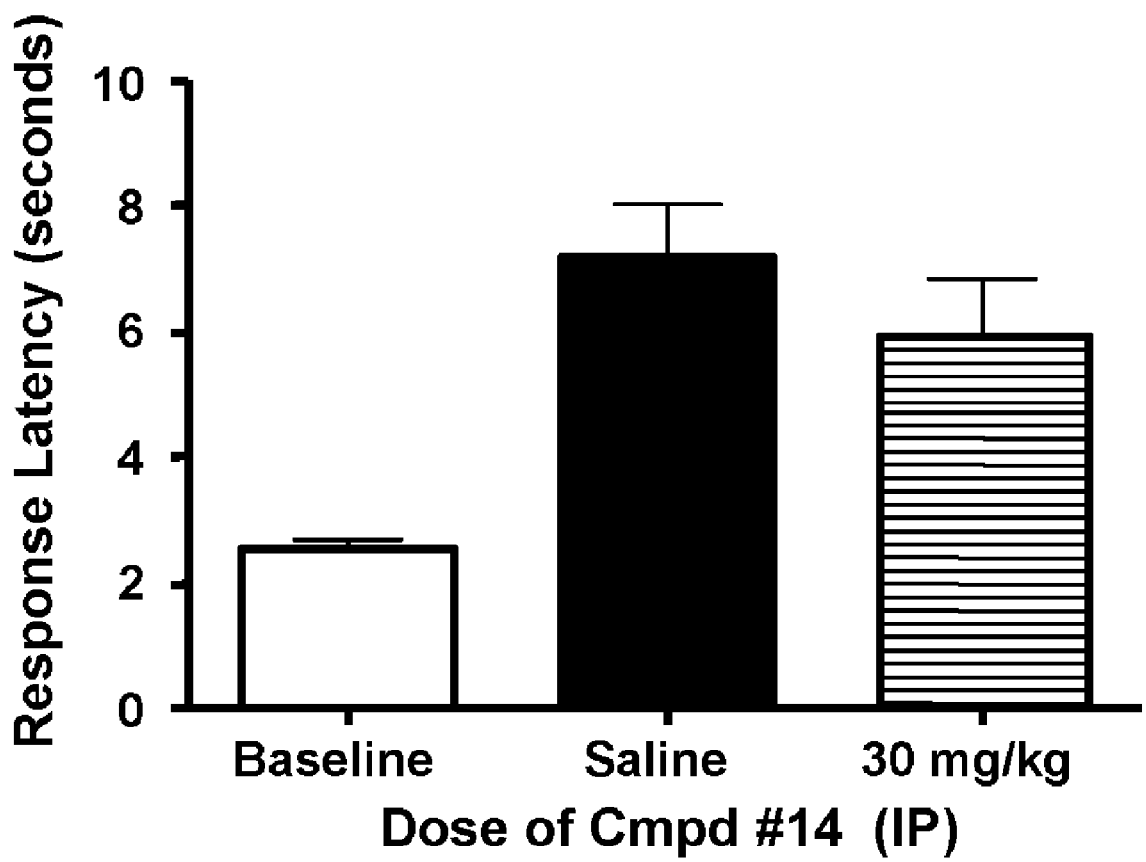
FIG. 8 is a graph of response latency (in seconds) vs. dose showing the effects on morphine-induced analgesia of Compound 14 in the tail flick test (intraperitoneal administration).
Figure 9:
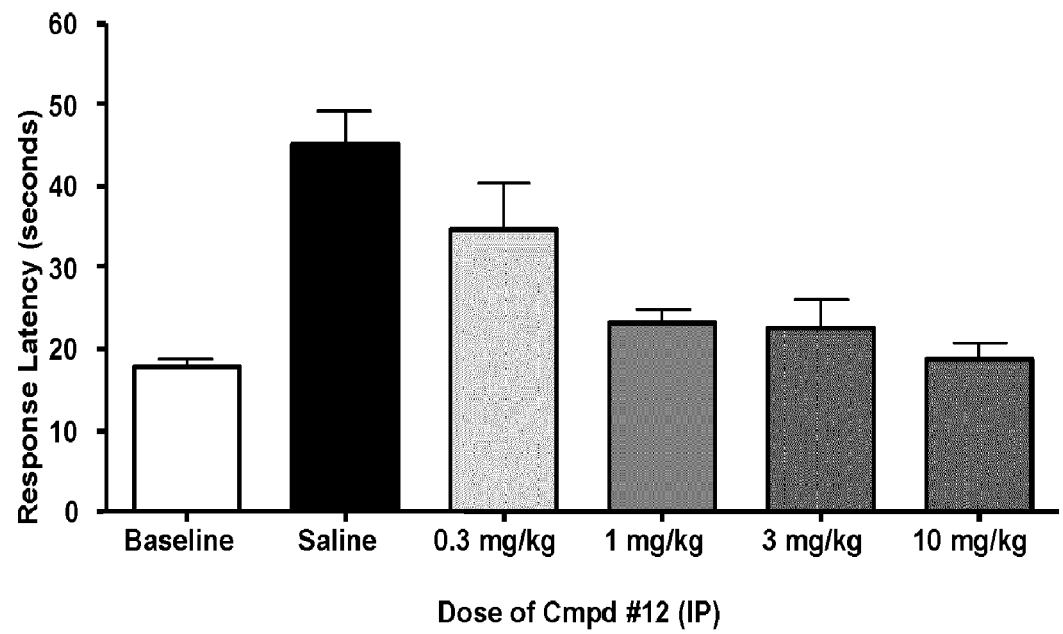
FIG. 9 is a graph of response latency (in seconds) vs. dose showing the effects on morphine-induced analgesia of Compound 12 in the hot plate test (intraperitoneal and oral administration).
Figure 9:
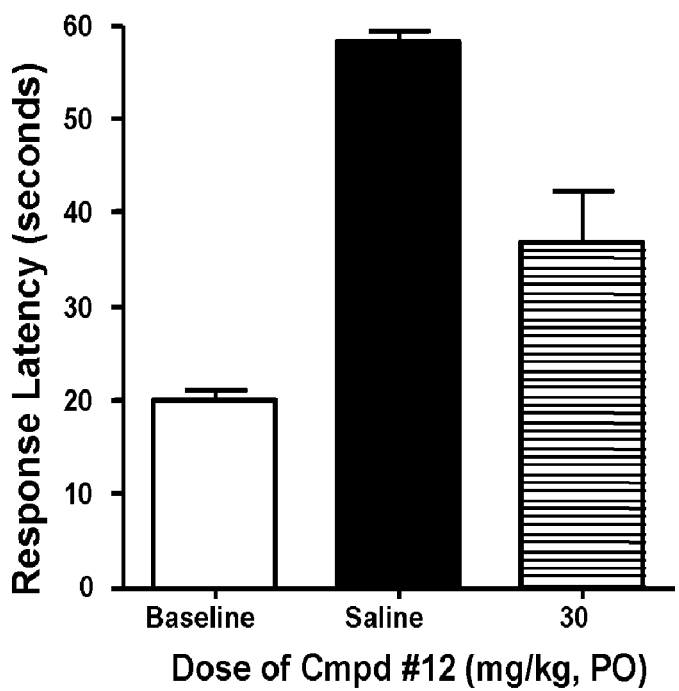
Figure 10:
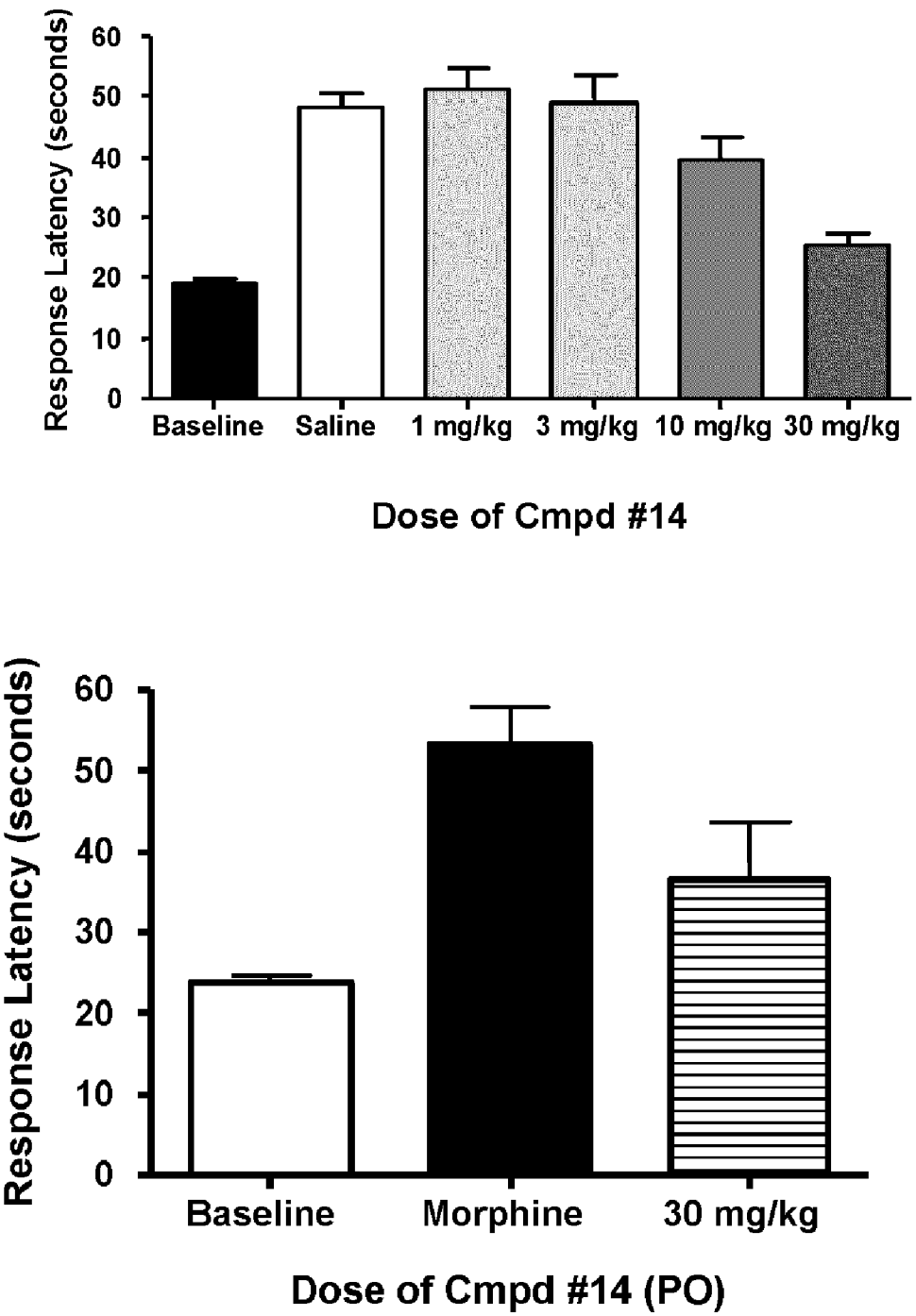
FIG. 10 is a graph of response latency (in seconds) vs. dose showing the effects on morphine-induced analgesia of Compound 14 in the hot plate test (intraperitoneal and oral administration).

Pharmacokinetic (PK) evaluation of Compound 6 in Rats. To investigate the possible relationship between the pharmacodynamic (PD) responses (ability to block effects of morphine in the 3 animal models used) and blood concentrations of Compound 6 following different routes, the absorption and clearance was studied in rats (FIG. 4). Rats were used for this study to allow for serial blood sampling after dose administration. It is believed that data from rats would be generally representative of PK mice. High bioavailability was observed following subcutaneous administration of Compound 6 relative to IV. However, the absorption of Compound 6 was low following oral administration. Again, these data support the concept that oral administration of this drug can have profound actions in reversing adverse effects of opioid compounds on the gastrointestinal tract, with a very low risk of adversely affecting the therapeutic analgesic properties of opioids.

Other Examples of Sample Compounds. Pharmacological profiles of Compounds 12 and 14 in rats using different routes of administration demonstrate that other compounds have similar effects in these models of gut motility and peripheral (tail flick) and central (hot plate) nociception (FIGS. 5-10).

It is important to note that the PGE$_2$ test is a model for peripheral activity, while the hot plate test is a model for central activity. The PGE$_2$ data for Compound 14 demonstrates that IP administration at 3 mg/kg reduces morphine's ability to block PGE$_2$-induced diarrhea (upward dose response curve), thereby suggesting peripheral activity. The hot plate test shows a shifted dose response curve, in that a statistical difference from baseline isn't seen until a dose of 30 mg/kg (3 to 10 times higher dose than required in the PGE$_2$ test), suggesting that Compound 14 has poor central activity. The tail flick test demonstrates similar results, with no statistical difference from baseline even at 30 mg/kg. The ideal peripheral antagonist affects only the gut (i.e., blocks diarrhea) but has little or no effect on blocking opioid analgesia (antinociception) in the mouse, either centrally (hot plate) or peripherally (tail flick).

The compounds of the invention are synthesized by the routes described below:

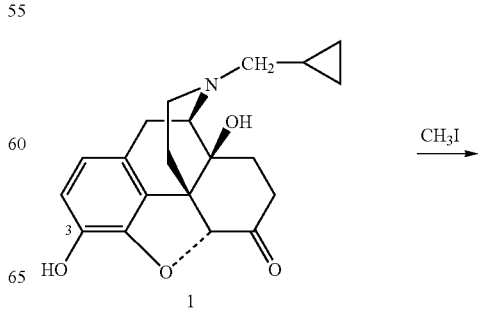

33
-continued
34
-continued
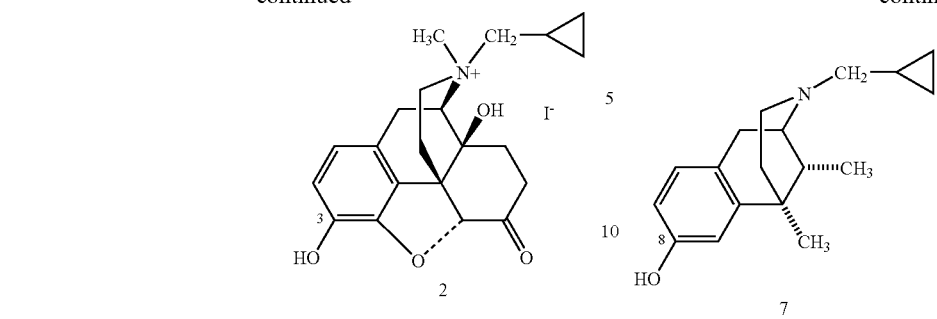
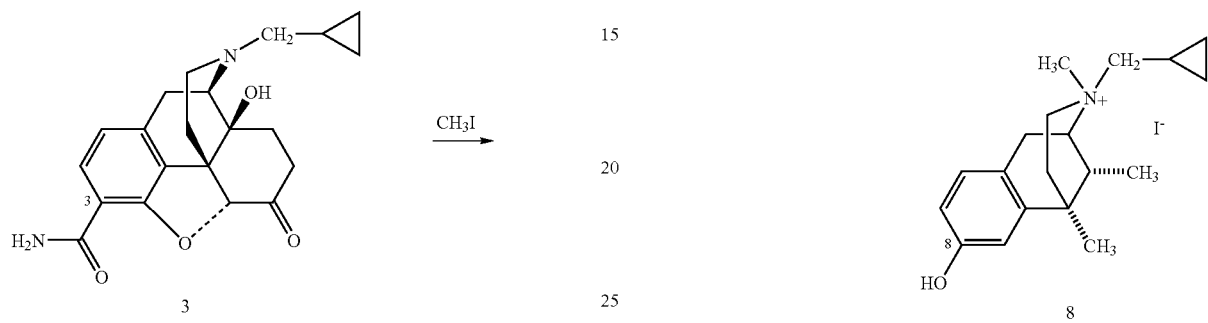
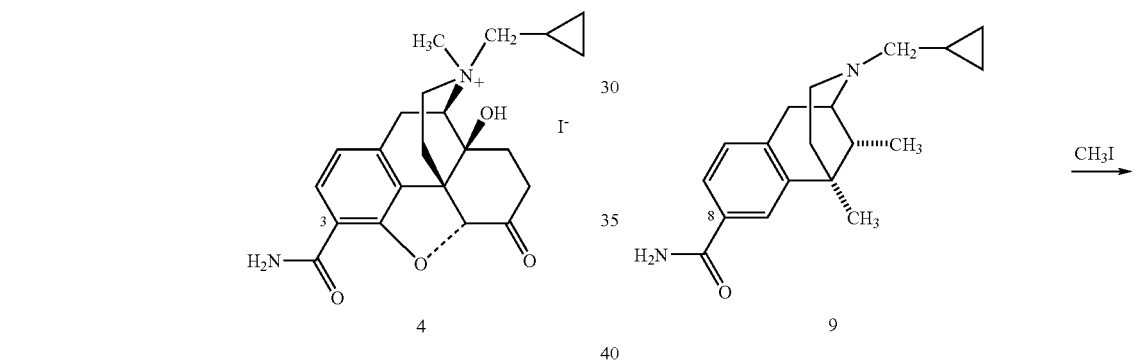
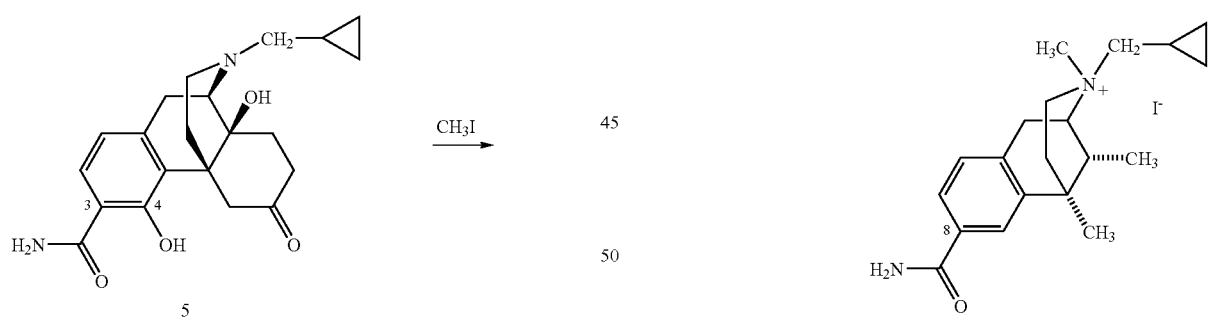
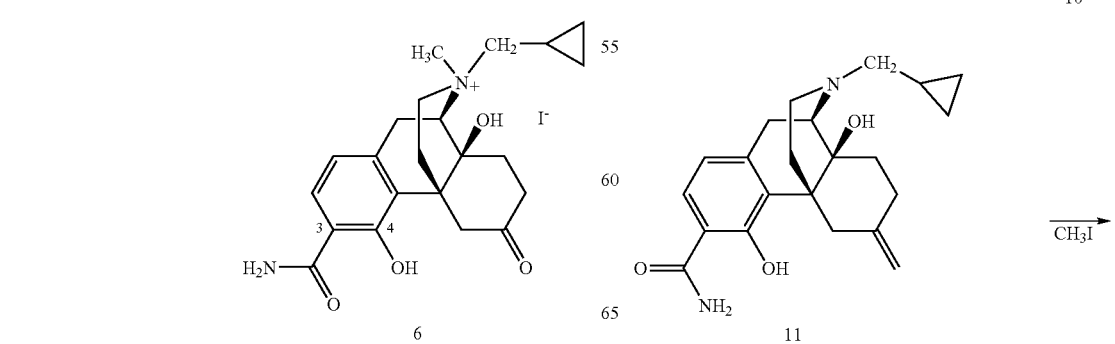

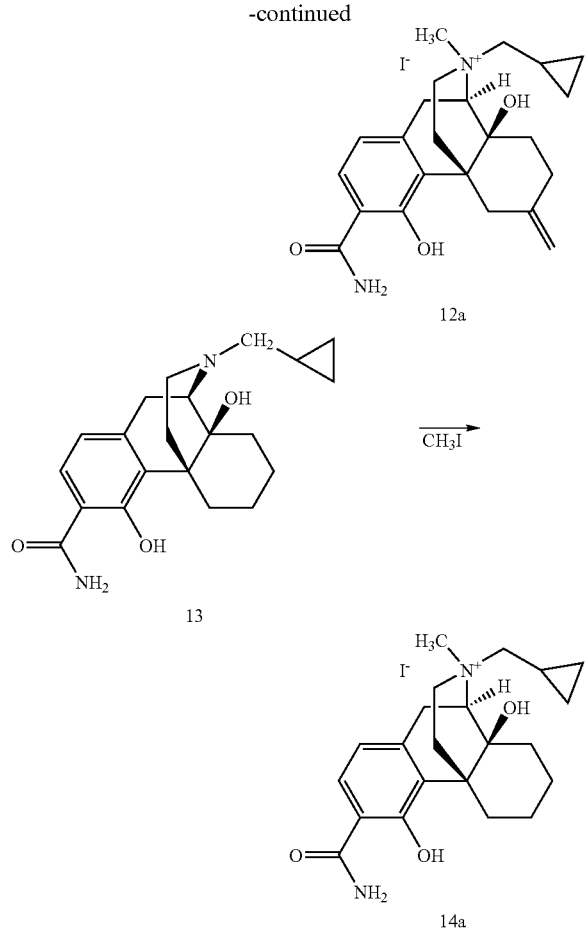

The I⁻ in the examples above and following can be exchanged for Cl⁻ using an ion exchange resin as described below. Similarly, Br⁻ could be exchanged for Cl⁻. A slurry of Dowex 1×8 resin-chloride form (25 g, 50-100 mesh) in deionized water is loaded into a glass chromatography column. Water is passed through until the pH of the solution is approximately 6-7. The compound to be exchanged is dissolved in water/methanol (1:2) and loaded onto the resin. The product-containing fractions are combined and the solvent is removed under reduced pressure (water bath 25° C.)

Proton NMR spectra and in certain cases $^{13}$C NMR were obtained on a Varian Unity-300 or 500 NMR spectrometer with tetramethylsilane as an internal reference for samples dissolved in CDCl$_3$. Samples dissolved in CD$_3$OD and DMSO-d$_6$ were referenced to the solvent. Proton NMR multiplicity data are denoted by s (singlet), d (doublet), t (triplet), q (quartet), m (multiplet), dd (doublet of doublets), and br (broad). Coupling constants are in hertz. Direct insertion probe chemical ionization mass spectral data were obtained on a Shimadzu GC-17A GC-MS mass spectrometer. Direct infusion electrospray ionization (in positively charged ion mode) mass spectral data were obtained on an Agilent 1100 series LC/MSD system (Germany). Melting points were determined on a Meltemp capillary melting point apparatus and were uncorrected. Infrared spectral data were obtained on a Perkin-Elmer Paragon 1000 FT-IR spectrophotometer. Optical rotation data was obtained from a Perkin-Elmer 241 polarimeter. The assigned structure of all test compounds and intermediates were consistent with the data. Carbon, hydrogen, and nitrogen elemental analyses for all novel targets were performed by Quantitative Technologies Inc., Whitehouse, N.J., and were within ±0.4% of theoretical values except as noted; the presence of water or other solvents was confirmed by proton NMR. Reactions were generally performed in an argon or nitrogen atmosphere. Commercially purchased chemicals were used without purification unless otherwise noted. The following reagents were purchased from Aldrich Chemical Company: N-hydroxysuccinimide, phenethylamine, 3-phenyl-1-propylamine, 4-aminobiphenyl, palladium acetate, 4-phenylbenzylamine and benzyl amine. The following reagent was purchased from Trans World Chemicals: 2-(4-biphenyl ethylamine). The following reagents were purchased from Strem Chemicals, Incorporated: 1,1'-bis(diphenylphosphino)ferrocene (dppf) and dichloro [1,1'-bis(diphenylphosphino)-ferrocene]palladium (II) dichloromethane adduct [PdCl$_2$(dppf)]. Pyridine was distilled from KOH. Amines were purchased from Aldrich Chemical Company and used as received unless otherwise indicated. Silica gel (Bodman Industries, ICN SiliTech 2-63 D 60A, 230-400 Mesh) was used for all flash chromatography. Toluene and Et$_2$O were distilled from sodium metal. THF was distilled from sodium/benzophenone ketyl. Pyridine was distilled from KOH. Methylene chloride was distilled from CaH$_2$. DMF and DMSO were distilled from CaH$_2$ under reduced pressure. Methanol was dried over 3 Å molecular sieves prior to use.

Naltrexone methiodide [2]. Naltrexone (1, 30 mg, 0.062 mmol) dissolved in 5 mL of dry acetone was added to iodomethane (0.04 mL, 0.62 mmol) in a reaction tube. The reaction tube was sealed and heated at 70° C. for four days. A white precipitate formed over the course of reaction. At the end of the reaction, the mixture was cooled and filtered and the precipitate was washed with cold acetone. The white precipitate was crystallized from methanol-ether to obtain the desired product 2 as a crystalline salt in 41% yield: mp 215-216° C. $^1$H NMR (DMSO-d6, 500 MHz) δ 9.52 (s, 1H) 6.67 (s, 2H), 6.35 (s, 1H), 4.90 (s, 1H), 4.02 (s, 1H), 3.91 (m, 2H), 3.62 (s, 3H), 3.52 (d, J=19.5 Hz, 1H), 3.05 (m, 1H), 2.92 (m, 2H), 2.76 (m, 2H), 2.10 (m, 1H), 1.97 (m, 1H), 1.59 (m, 2H), 1.22 (m, 1H), 0.77 (m, 1H), 0.70 (m, 1H), 0.61 (m, 1H), 0.37 (m, 1H). MS m/z 356 [(M−I−)+]. Anal. Calcd for C$_{21}$H$_{26}$IN4.0.75H$_2$O: C, 50.77; H, 5.58; N, 2.82. Found C, 50.49; H, 5.70; N, 2.71.

2D NOESY (DMSO-d6, 500 MHz, Mixing time=0.6 sec, Relax. delay=0.9 sec): A cross peak was observed between the proton of 14-OH group and the protons of CH$_3$ group connected to quaternized nitrogen. This demonstrates that the CH$_3$ group occupies the axial conformation with respect the 6-membered piperidine ring, thereby putting the cyclopropyl methyl group in the equatorial position.

Using a similar procedure the following N-methyl quaternaries were synthesized starting from the corresponding base compound:

3-Carboxamido-naltrexone methiodide [4] was obtained from 3 as a white crystalline solid in 43% yield: mp 189-190° C. $^1$H NMR (DMSO-d6, 500 MHz) δ 7.77 (s, 1H), 7.66 (d, J=8.0 Hz, 1H), 7.07 (s, 1H), 7.00 (d, J=8.0 Hz, 1H), 6.46 (s, 1H), 5.29 (s, 1H), 3.99 (m, 2H), 3.71 (d, J=21.0 Hz, 1H), 3.65 (s, 3H), 3.28 (m, 2H), 2.97 (m, 2H), 2.79 (m, 2H), 2.14 (d, J=14.5 Hz, 1H), 2.02 (d, J=11.5 Hz, 1H), 1.71 (d, J=12.5 Hz, 1H), 1.55 (m, 2H), 1.24 (m, 1H), 0.79 (m, 1H), 0.73 (m, 1H), 0.62 (m, 1H), 0.40 (m, 1H). MS m/z 383 [(M−I−)+]. Anal. Calcd for C$_{22}$H$_{27}$IN$_2$O$_4$.0.75H$_2$O: C, 50.44; H, 5.48; N, 5.35. Found C, 50.28; H, 5.42; N, 5.24.

3-Carboxamido-4-hydroxy-naltrexone methiodide [6] was obtained from 5 as a white crystalline solid in 60% yield: mp 197-198° C. $^1$H NMR (DMSO-d6, 500 MHz) 14.50 (s, 1H), δ 8.48 (s, 1H), 8.01 (s, 1H), 7.75 (d, J=8.5 Hz, 1H), 6.76 (d, J=8.0 Hz, 1H), 6.20 (s, 1H), 3.90 (m, 2H), 3.80 (m, 1H), 3.59 (s, 3H), 3.45 (s, 2H), 3.27 (m, 1H), 2.95 (m, 1H), 2.80 (d, J=14.0 Hz, 1H), 2.65 (m, 2H), 2.46 (m, 1H), 2.01 (m, 3H), 1.80 (d, J=14 Hz, 1H), 1.21 (m, 1H), 0.77 (m, 1H), 0.70 (m, 1H), 0.59 (m, 1H), 0.38 (m, 1H). MS m/z 385 [(M−I−)+]. Anal. Calcd for $C_{22}H_{29}IN_2O_4$·0.1$H_2O$: C, 51.57; H, 5.70; N, 5.47. Found C, 51.39; H, 5.72; N, 5.45.

2D NOESY (DMSO-d6, 500 MHz, Mixing time=0.6 sec, Relax. delay=0.9 sec): A cross peak was observed between the proton of 14-OH group and the protons of $CH_3$ group connected to quaternized nitrogen. This demonstrates that the $CH_3$ group occupies the axial conformation with respect the 6-membered piperidine ring, thereby putting the cyclopropyl methyl group in the equatorial position.

Cyclazocine methiodide [8] was obtained was obtained from 7 as a white crystalline solid in 74% yield: mp 165-168° C. $^1$H NMR (DMSO-d6, 500 MHz) δ 9.20 (s, 1H), 6.99 (d, J=8.5 Hz, 1H), 6.67 (d, J=2.5 Hz, 1H), 6.64 (dd, 1H), 3.77 (s, 1H), 3.68 (dd, 1H), 3.32 (s, 3H), 3.29 (m, 1H), 3.19-3.06 (m, 3H), 2.66 (m, 1H), 2.47 (m, 1H), 2.21 (m, 1H), 1.40 (m, 1H), 1.36 (s, 3H), 1.16 (m, 1H), 0.84 (d, J=6.5 Hz, 3H), 0.74-0.70 (m, 2H), 0.52-0.50 (m, 1H), 0.40-0.37 (m, 1H). MS m/z 286 [(M−I−)+].

8-Carboxamido-cyclazocine methiodide [10] was obtained was obtained from 9 as a white crystalline solid in 70% yield: mp 237-238° C. $^1$H NMR (DMSO-d6, 500 MHz) δ 7.95 (s, 1H), 7.81 (s, 1H), 7.73 (d, J=7.5 Hz, 1H), 7.33 (s, 1H), 7.26 (d, J=8.5 Hz, 1H), 3.84 (s, 1H), 3.72 (m, 1H), 3.33 (s, 3H), 3.29 (m, 1H), 3.25-3.11 (m, 3H), 2.59-2.53 (m, 2H), 2.28 (m, 1H), 1.47 (s, 3H), 1.45 (m, 1H), 1.17 (m, 1H), 0.83 (d, J=7.0 Hz, 3H), 0.75-0.69 (m, 2H), 0.52-0.50 (m, 1H), 0.42-0.40 (m, 1H). MS m/z 313 [(M−I−)+].

(5a)-17-(Cyclopropylmethyl)-14-hydroxy-6-oxo-4,5-epoxymorphinan-3-yl trifluoromethanesulfonate [P1]: To an ice/water cooled solution of Naltrexone (30.0 g, 87.9 mmol), and triethylamine (36.75 mL, 87.9 mmol) in DCM (1L) was added N-phenylbis(trifluoromethanesulfonamide). The reaction was stirred at room temperature for 18 hours. The mixture was concentrated under reduced pressure (approximately 500 mL) and washed with 7% ammonium hydroxide (400 mL). The organic phase was washed with a 2N sodium carbonate solution until none of the triflating reagent remained (8 L in total). The organic phase was dried ($MgSO_4$). Filtration and removal of the solvent under reduced pressure gave (5a)-17-(cyclopropylmethyl)-14-hydroxy-6-oxo-4,5-epoxymorphinan-3-yl trifluoromethanesulfonate [P1] (38.0 g, 91% yield); LC/MS 474 (M+H)+.

(5a)-17-(Cyclopropylmethyl)-14-hydroxy-6-oxo-4,5-epoxymorphinan-3-carbonitrile [P2]: A mixture of (5a)-17-(cyclopropylmethyl)-14-hydroxy-6-oxo-4,5-epoxymorphinan-3-yl trifluoromethanesulfonate [P1] (38.0 g, 80.3 mmol), zinc cyanide (18.85 g, 160.5 mmol), and tetrakis(triphenylphosphine)palladium(0) (8.5 g, 7.36 mmol) in DMF (500 mL—degassed with argon for 3 hours) was heated at 120° C. under argon for 3 hours. The reaction mixture was allowed to return to room temperature then diluted with ethyl acetate (1L) and passed through a pad of celite. The solution was washed with water (3×1 L) and the organic phase dried ($MgSO_4$). Filtration and removal of the solvent under reduced pressure gave crude product that was triturated with methanol to give (5a)-17-(cyclopropylmethyl)-14-hydroxy-6-oxo-4,5-epoxymorphinan-3-carbonitrile [P2] (17.12 g, 61% yield); LC/MS (r.t. 12.7 minutes [5 to 95% B]), 351 (M+H)+.

(5a)-17-(Cyclopropylmethyl)-14-hydroxy-6-oxo-4,5-epoxymorphinan-3-carboxamide [P3]: To an ice/water cooled suspension of (5a)-17-(cyclopropylmethyl)-14-hydroxy-6-oxo-4,5-epoxymorphinan-3-carbonitrile [P2] (6.0 g, 17.1 mmol) and potassium carbonate (7.09 g, 51.37 mmol) in DMSO (120 mL) was added hydrogen peroxide (25 mL, 35 wt. % in $H_2O$) drop wise at a rate to ensure the temperature remained below 20° C. The mixture was stirred for 2 hours then diluted with DCM (800 mL). The solution was washed with water (3×500 mL) before the organic phase was dried ($MgSO_4$). Filtration and removal of the solvent under reduced pressure gave crude product that was purified by trituration with methanol giving (5a)-17-(cyclopropylmethyl)-14-hydroxy-6-oxo-4,5-epoxymorphinan-3-carboxamide [P3] (4.50 g, 71% yield); LC/MS (r.t. 10.1 minutes [5 to 95% B]), 369 (M+H)+.

17-(cyclopropylmethyl)-4,14-dihydroxy-6-oxomorphinan-3-carboxamide [P4]: A mixture of (5a)-17-(cyclopropylmethyl)-14-hydroxy-6-oxo-4,5-epoxymorphinan-3-carboxamide [P3] (3.0 g, 8.15 mmol), Zinc powder (2.67 g, 40.76 mmol), and ammonium chloride (3.05 g, 57.1 mmol) in ethanol (500 mL) was heated at 90° C. for 1 hour. The reaction mixture was allowed to return to room temperature then filtered. The residual solid was washed with excess methanol (500 mL) followed by 7% ammonium hydroxide (100 mL). The combined filtrates were concentrated under reduced pressure and the residue partitioned between dichloromethane and 7% ammonium hydroxide solution. The aqueous phase was washed with further DCM and the combined organic layers dried ($MgSO_4$). Filtration and removal of the solvent under reduced pressure giving 117-(cyclopropylmethyl)-4,14-dihydroxy-6-oxomorphinan-3-carboxamide [P4] (1.45 g, 48% yield); LC/MS (r.t. 10.7 minutes [5 to 95% B]), 371 (M+H)+.

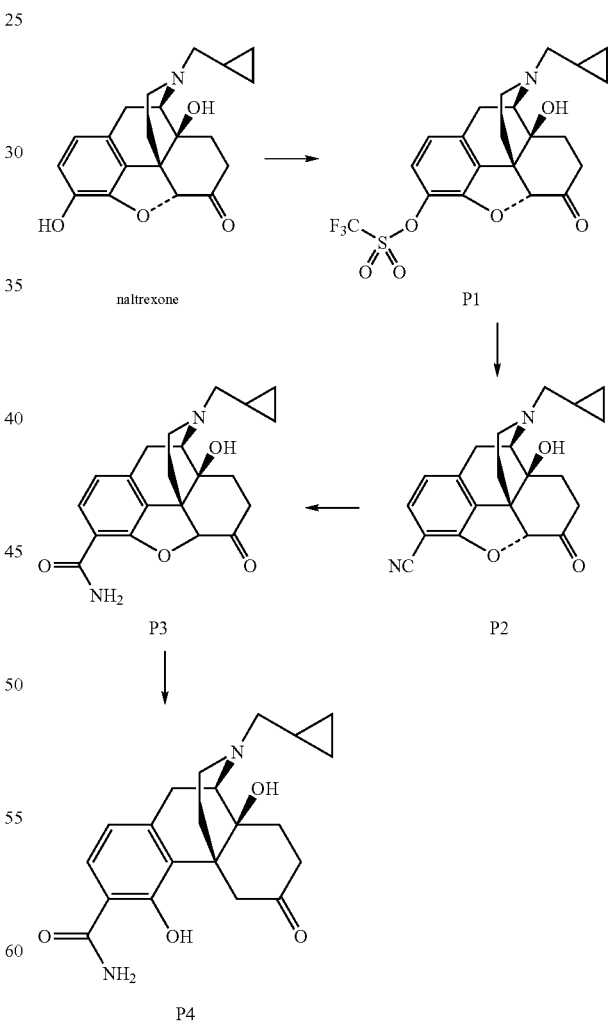

17-(Cyclopropylmethyl)-4,14-dihydroxy-6-methylenemorphinan-3-carboxamide [11]: Sodium hydride (324 mg, 8.1 mmol, 60% dispersion in mineral oil) was washed under an argon atmosphere with hexane. DMSO (5 mL) was added and the mixture heated at 60° C. for 1 hour. Methyltriphenylphosphonium bromide (2.89 g, 8.1 mmol) was added and stirred at the same temperature for 1 hour. A solution of 17-(cyclopropylmethyl)-4,14-dihydroxy-6-oxomorphinan-3-carboxamide [P4] (0.6 g, 1.62 mmol) in DMSO (10 mL) was added and the mixture heated at 65° C. for 42 hours (A further 5 equivalents of Wittig reagent was added after 18 hours). The reaction was allowed to return to room temperature and partitioned between ethyl acetate (300 mL) and water (300 mL). The organic phase was washed with brine and dried ($MgSO_4$). Filtration and removal of the solvent under reduced pressure gave a residue that was stirred with hydrochloric acid (5%) for 30 minutes before washing with ethyl acetate. The aqueous phase was adjusted to pH8 by the addition of 2N sodium hydroxide solution and then extracted with DCM and dried ($MgSO_4$). Filtration and removal of the solvent under reduced pressure gave a residue that was purified by prep-HPLC [Xbridge Prep C18 OBD, 30×150 mm, 5 µm; Mobile Phase A: 10 mM $NH_4HCO_3$ (pH10), Phase B: MeCN; Flow: 50 ml/min; Column Temperature: 30° C.; Runtime: 25 min.] giving 17-(cyclopropylmethyl)-4,14-dihydroxy-6-methylenemorphinan-3-carboxamide [11] (180 mg, 30% yield); LC/MS (r.t. 13.3 minutes [5 to 95% B]), 369 $(M+H)^+$.

(17R)-17-(Cyclopropylmethyl)-4,14-dihydroxy-17-methyl-6-methylenemorphinan-17-ium-3-carboxamide chloride (12) was obtained from 11 in a 44% yield. To a mixture of 17-(cyclopropylmethyl)-4,14-dihydroxy-6-methylenemorphinan-3-carboxamide [11] (519 mg, 1.41 mmol) in acetonitrile (5 mL) was added iodomethane (1.0 mL, 16.1 mmol). The tube was sealed and the reaction heated at 90° C. for 18 hours. The reaction mixture was allowed to cool to room temperature and the solid isolated by filtration, washed with further acetonitrile (10 mL), then dried under reduced pressure (50° C.). A slurry of Dowex 1×8 resin-chloride form (25 g, 50-100 mesh) in de-ionized water was loaded into a glass chromatography column. Water was passed through until the pH of the solution was around 6-7. The compound (439 mg, 0.86 mmol) was dissolved in methanol and loaded onto the resin. The product-containing fractions were combined and the solvent removed under reduced pressure (water bath 25° C.) giving (17R)-17-(cyclopropylmethyl)-4,14-dihydroxy-17-methyl-6-methylenemorphinan-17-ium-3-carboxamide chloride [12] (262 mg, 44% yield); LC/MS (r.t. 7.2 minutes [5 to 95% B]), 383 $(M)^+$. Exact mass=418.20; molecular weight=418.96.

17-(Cyclopropylmethyl)-4,14-dihydroxymorphinan-3-carboxamide [1,3]: To a mixture of (5a)-17-(cyclopropylmethyl)-14-hydroxy-6-oxo-4,5-epoxymorphinan-3-carboxamide [P3] (3.74 g, 10.2 mmol) and zinc powder (33.0 g, 0.51 mol) in acetic acid (220 mL) was added 12N HCl (30 mL). The reaction was heated at 125° C. for 3 hours then allowed to return to room temperature. The mixture was slowly quenched into an ice/water cooled ammonium hydroxide solution at such a rate to ensure the temperature remained below 20° C. The resultant suspension was extracted with DCM (3×500 mL) and dried ($MgSO_4$). Filtration and removal of the solvent under reduced pressure gave the crude product that was purified by prep-HPLC [Xbridge Prep C18 OBD, 30×150 mm, 5 µm; Mobile Phase A: 10 mM $NH_4HCO_3$ (pH 10), Phase B: MeCN; Flow: 50 ml/min; Column Temperature: 30° C.; Runtime: 25 min.] giving 17-(cyclopropylmethyl)-4,14-dihydroxymorphinan-3-carboxamide [13] (1.07 g, 29% yield); LC/MS (r.t. 10.2 minutes [5 to 95% B]), 357 $(M+H)^+$.

(17R)-17-(Cyclopropylmethyl)-4,14-dihydroxy-17-methylmorphinan-17-ium-3-carboxamide chloride (14) was obtained from 13 in a 67% yield. To a mixture of 17-(cyclopropylmethyl)-4,14-dihydroxymorphinan-3-carboxamide [13] (260 mg, 0.73 mmol) in acetonitrile (5 mL) was added iodomethane (1.0 mL, 16.1 mmol). The tube was sealed and the reaction heated at 90° C. for 18 hours. The reaction mixture was allowed to cool to room temperature and the solid isolated by filtration, washed with further acetonitrile (10 mL), then dried under reduced pressure (50° C.). A slurry of Dowex 1×8 resin-chloride form (25 g, 50-100 mesh) in de-ionized water was loaded into a glass chromatography column. Water was passed through until the pH of the solution was around 6-7. The compound (312 mg, 0.63 mmol) was dissolved in water/methanol (1:2) and loaded onto the resin. The product-containing fractions were combined and the solvent removed under reduced pressure (water bath 25° C.) giving (17R)-17-(cyclopropylmethyl)-4,14-dihydroxy-17-methylmorphinan-17-ium-3-carboxamide chloride [1,4] (199 mg, 67% yield); LC/MS (r.t. 6.7 minutes [5 to 50% B]), 371 $(M)^+$. Exact mass=406.20; molecular weight=406.95.

Alternative method for [6] (chloride): To a mixture of 17-(cyclopropylmethyl)-4,14-dihydroxy-6-oxomorphinan-3-carboxamide [P4] (1 g, 2.7 mmol) in acetonitrile (5 mL) was added iodomethane (1.7 mL, 27 mmol). The tube was sealed and the reaction heated at 90° C. for 18 hours. The reaction mixture was allowed to cool to room temperature and the solid isolated by filtration, washed with further acetonitrile (10 mL), then dried under reduced pressure (50° C.). A slurry of Dowex 1×8 resin-chloride form (20 g, 50-100 mesh) in de-ionised water was loaded into a glass chromatography column. Water was passed through until the pH of the solution was around 6-7. The compound (0.61 g, 1.19 mmol) was dissolved in water/methanol (1:2) and loaded onto the resin. The product containing fractions were combined and the solvent removed under reduced pressure (water bath 3 0° C.) giving (17R)-17-(cyclopropylmethyl)-4,14-dihydroxy-17-methyl-6-oxomorphinan-17-ium-3-carboxamide chloride [6 ($Cl^-$)] (0.44 g, 87% yield); LC/MS (r.t. 9.6 minutes [0 to 20% B]), 385 $(M)^+$.

Alternative method for [4] (chloride): To a suspension of (5a)-17-(cyclopropylmethyl)-14-hydroxy-6-oxo-4,5-epoxymorphinan-3-carboxamide [P3] (0.75 g, 2.0 mmol) in acetonitrile (5 mL) was added iodomethane (1.2 mL, 19.3 mmol). The tube was sealed and the reaction heated at 90° C. for 18 hours. Further iodomethane (1 mL, 16.1 mmol) was added and the mixture heated for 24 hours. The reaction mixture was allowed to cool to room temperature and the solid isolated by filtration, washed with further acetonitrile (10 mL), then dried under reduced pressure (50° C.). A slurry of Dowex 1×8 resin-chloride form (20 g, 50-100 mesh) in de-ionised water was loaded into a glass chromatography column. Water was passed through until the pH of the solution was around 6-7. The compound (0.40 g, 0.78 mmol) was dissolved in water/methanol (1:1) and loaded onto the resin. The product containing fractions were combined and the solvent removed under reduced pressure (water bath 30° C.) giving (5 a, 17R)-17-(cyclopropylmethyl)-14-hydroxy-17-methyl-6-oxo-4,5-epoxymorphinan-17-ium-3-carboxamide chloride [4 ($Cl^-$)] (0.22 g, 67% yield); LC/MS (r.t. 5.4 minutes [5 to 50% B]), 383 $(M)^+$.

In general, the chemistry described above works in the presence of the variety of functional groups found on known core structures. The exceptions would be morphine and congeners having a free 6-OH, which can be protected by a TBDPS (t-butyldiphenylsilyl) group [see Wentland et al., "Selective Protection and Functionalization of Morphine . . . ", J. Med. Chem. 43, 3558-3565 (2000)].

Further compounds of the invention also include:

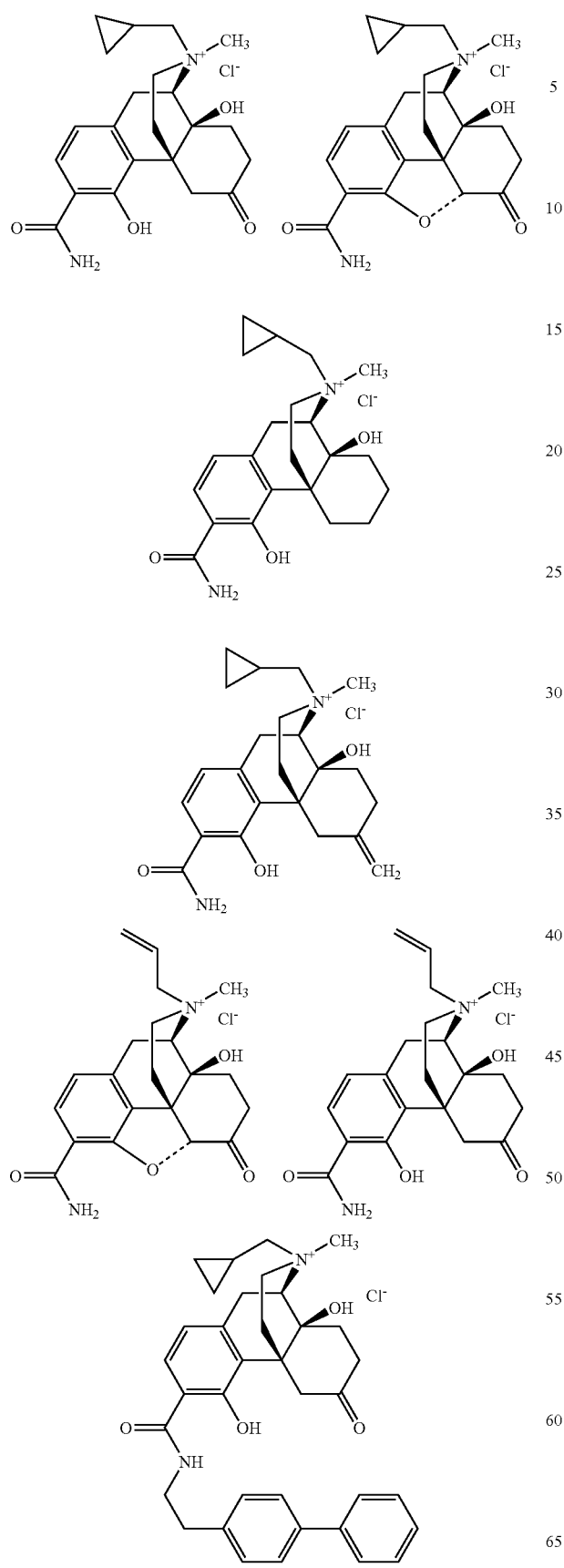
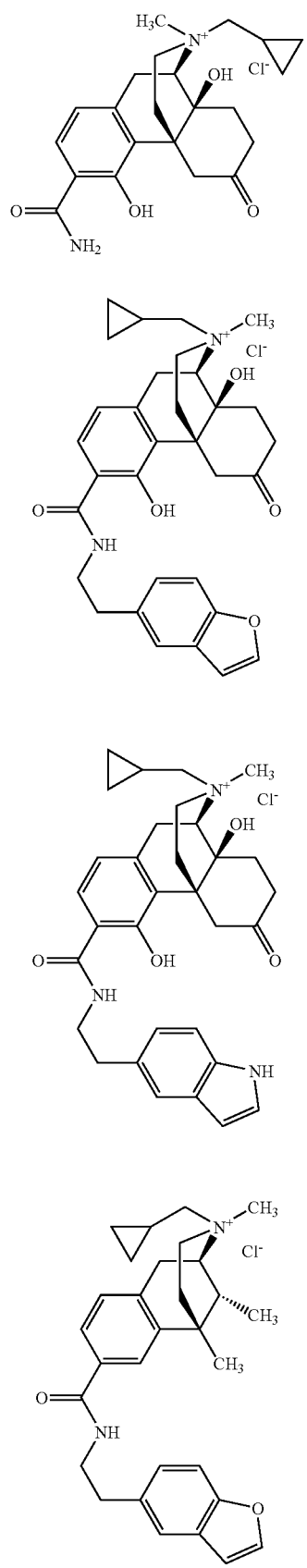

-continued
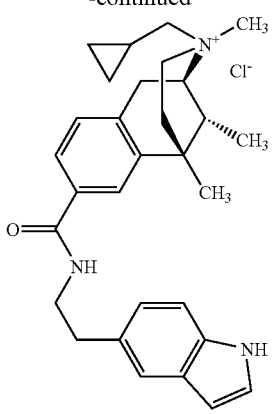
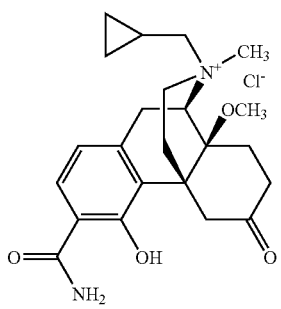
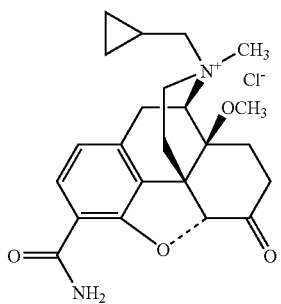
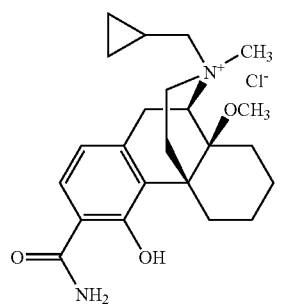
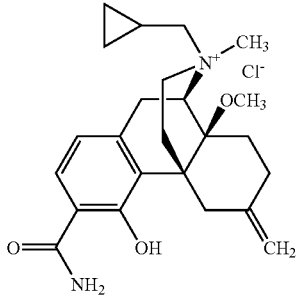
-continued
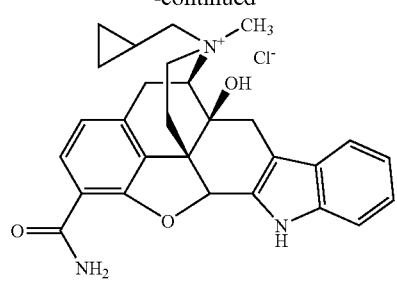
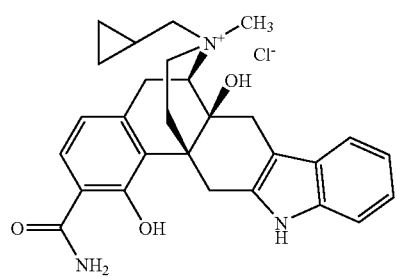
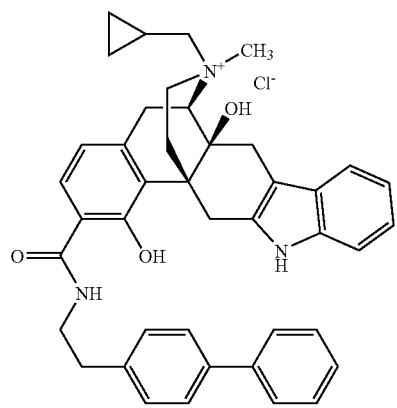
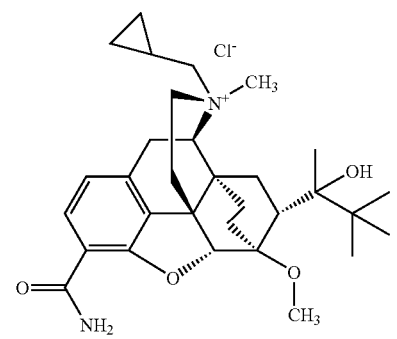

45

46

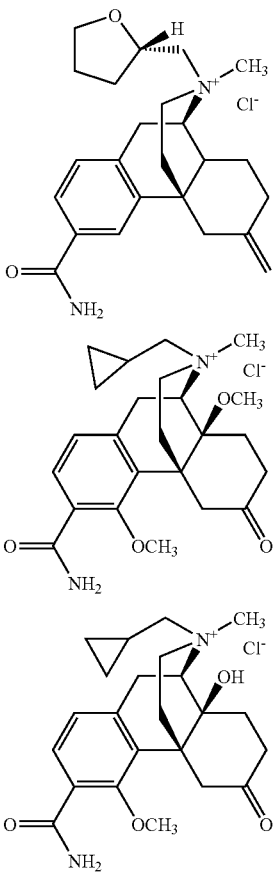
as well as the corresponding ethyl, propyl and butyl quaternary ammoniums and their chlorides and other salts.
What is claimed is:
1. A compound of formula
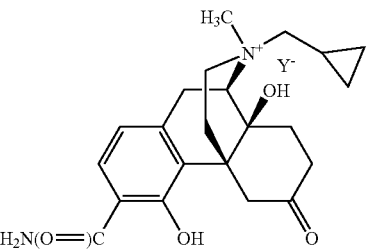
wherein Y is a counterion.
2. A compound having the formula:
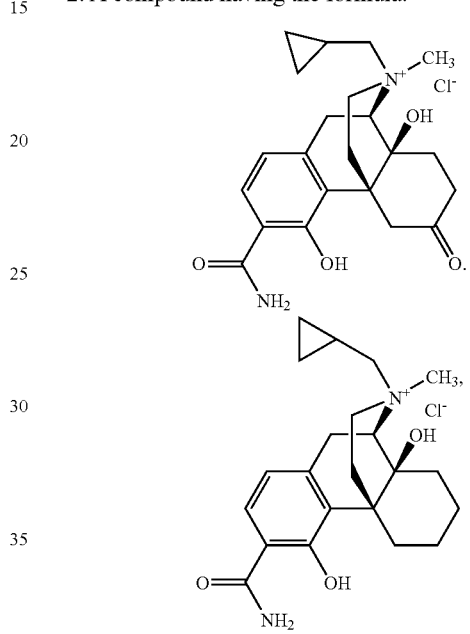
* * * * *

UNITED STATES PATENT AND TRADEMARK OFFICE
CERTIFICATE OF CORRECTION

PATENT NO. : 8,263,807 B2
APPLICATION NO. : 12/188814
DATED : September 11, 2012
INVENTOR(S) : Mark P. Wentland Page 1 of 1

It is certified that error appears in the above-identified patent and that said Letters Patent is hereby corrected as shown below:

Column 48, Lines 15 to 35: Claim 2, Delete

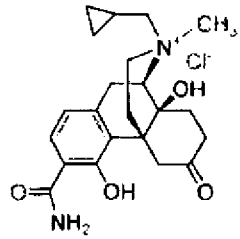

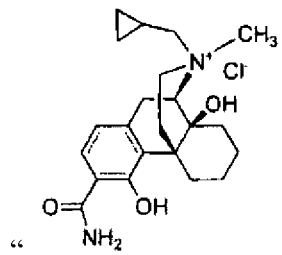

" " and insert

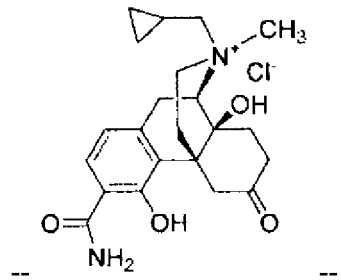

-- --

Signed and Sealed this
First Day of January, 2013

David J. Kappos
Director of the United States Patent and Trademark Office